(12) United States Patent
Subash et al.

(10) Patent No.: US 8,311,848 B2
(45) Date of Patent: Nov. 13, 2012

(54) ELECTRONIC MEDICAL RECORD CREATION AND RETRIEVAL SYSTEM

(76) Inventors: Muthiah Subash, Bettendorf, IA (US); Ilesh Kurani, Moline, IL (US); Brian Kingsbury, Davenport, IA (US)

( * ) Notice: Subject to any disclaimer, the term of this patent is extended or adjusted under 35 U.S.C. 154(b) by 142 days.

(21) Appl. No.: 12/861,563

(22) Filed: Aug. 23, 2010

(65) Prior Publication Data

US 2011/0082710 A1    Apr. 7, 2011

Related U.S. Application Data

(60) Provisional application No. 61/248,741, filed on Oct. 5, 2009.

(51) Int. Cl.
*G06Q 50/00* (2006.01)

(52) U.S. Cl. .................................. 705/2; 705/3
(58) Field of Classification Search .................... 705/2, 3
See application file for complete search history.

(56) References Cited

U.S. PATENT DOCUMENTS

| | | | |
|---|---|---|---|
| 6,047,259 A * | 4/2000 | Campbell et al. | 705/3 |
| 6,383,135 B1 * | 5/2002 | Chikovani et al. | 600/300 |
| 6,684,188 B1 | 1/2004 | Mitchell et al. | 705/3 |
| 6,684,276 B2 | 1/2004 | Walker et al. | 710/73 |
| 7,197,492 B2 | 3/2007 | Sullivan | 707/2 |
| 7,962,348 B2 * | 6/2011 | Dew et al. | 705/2 |
| 8,046,241 B1 * | 10/2011 | Dodson | 705/2 |
| 2001/0041992 A1 | 11/2001 | Lewis et al. | 705/3 |
| 2003/0120516 A1 | 6/2003 | Perednia | 705/3 |
| 2003/0146942 A1 * | 8/2003 | Helgason et al. | 345/968 |
| 2004/0078215 A1 * | 4/2004 | Dahlin et al. | 705/2 |
| 2004/0122308 A1 * | 6/2004 | Ding | 600/407 |
| 2004/0236608 A1 | 11/2004 | Ruggio et al. | 705/2 |
| 2005/0171762 A1 | 8/2005 | Ryan et al. | 704/200 |
| 2005/0209890 A1 | 9/2005 | Kong | 705/3 |
| 2006/0020886 A1 | 1/2006 | Agrawal et al. | 715/530 |
| 2006/0116908 A1 | 6/2006 | Dew et al. | 705/2 |
| 2006/0173858 A1 | 8/2006 | Cantlin et al. | 707/10 |
| 2006/0235280 A1 | 10/2006 | Vonk et al. | 600/300 |
| 2006/0241977 A1 | 10/2006 | Fitzgerald et al. | 705/3 |
| 2009/0192823 A1 * | 7/2009 | Hawkins et al. | 705/3 |
| 2010/0050110 A1 * | 2/2010 | Hughes et al. | 715/781 |

* cited by examiner

*Primary Examiner* — Gerald J. O'Connor
*Assistant Examiner* — Neha Patel
(74) *Attorney, Agent, or Firm* — Brinks Hofer Gilson & Lione

(57) ABSTRACT

An electronic medical record system enables organic growth of medical conditions or choices linked to predefined human body systems or an anatomical image. These choices are used as blue print launchers that form sentences/paragraphs as a user interacts with the choice lists. The choice lists can include a set of control variables that can be selected to create a medical history of a patient in the form of one or more visit notes. The medical history of the patient is formed by user selection of some of the control variables for insertion into fillable data entry locations in the sentences/paragraphs. The sentences/paragraphs are in the form of blue prints which are available generically to be populated with patient specific information to form customized blue prints for a particular patient. Multiple data perspectives in the electronic medical record system allows relatively easy and simultaneous collection of the complex medical data to produce medical visit notes or letters during a patient office visit.

23 Claims, 15 Drawing Sheets

| Subjective | |
|---|---|
| CC&HP1 ▶ | |

| | | | | |
|---|---|---|---|---|
| | ⚲ Test, Male | | | |
| Fup ▶ | Select Room | Waiting Room ▶ | Urgency Level | Normal ▶ | Current Status | Checked in/Nurse Triage ▶ |
| History ▶ | ⦿ All Templates ○ My Templates | | | |
| PMH ▶ | ⦿ Selection ○ Anatomy ○ Symptoms | 1501 | 1502 | |
| PSH ▶ | Allergic Rhinitis (Allergic Rhinitis) | Select | | SOAP notes |
| FH ▶ | Chief complaints – CVS (CVS) | apneic episode at night | | |
| Meds ▶ | Chief complaints – Data Entry (Dataentry) | calf cramps | | Chief Complaints |
| Alrg ▶ | Chief Complaints – Endocrine (Endocrine) | calf pain | | CVS - BP |
| SH ▶ | Chief Complaints – ENT (ENT) | chest discomfort | | ⌐1503 |
| ROS ▶ | Chief Complaints – GI (GI) | chest pain | | |
| | Chief Complaints – Injections (Injections) | chest tightness | | |
| | Chief Complaints – Musculo (Muscular) | cough | | |
| | Chief Complaints – Neuro (Neuro) | distention of the abdomen | | |
| | Chief Complaints – Pulmonary (Pulmonary) | dizziness | | |
| | diarrhea (Diarrhea) | dyspnea on exertion | | |
| | diarrhea (Gastrointesinal System) | fainting | | |
| | Evaluation List – CVS (CVS) | fainting/blacking out | | |
| | Evaluation List – Endocrine (Endocrine) | fatigue | | |
| | Evaluation List – ENT (ENT) | heartburn | | |
| | Evaluation List – Neuro (Neuro) | hypertension | | |
| | Evaluation List – Pulmonary (Pulmonary) | intermittent claudication | | |
| | Follow up – CC&HPI (Follow up – CC&HPI) | leg pain | | |
| | Headache (Headache) | leg swelling | | |
| | Hearing loss – Complaints (Hearing loss) | nausea | | |
| | Heart Failure (Heart Failure) | night cramps | | |
| | Hypertension (Hypertension) | orthopnea | | |
| | Hypothyroidism (Hpothyroidism) | palpitation | | |
| | Insomnia Chief Complaints (Insomnia) | PND (paroxysmal nocturnal dyspnea) | | |
| | Musculoskeletal (Muscular) | shortness of breath | | |
| | Nosebleed (Nosebleed) | snoring | | |
| | Type 2 diabetes (Type 2 diabetes) | sputum production | | |
| | | stroke like or TIA like symptoms | | |
| Subjective | | sweating | | |
| Objective | | swelling of the feet | | |
| Assessment | | syncope | | |
| Planning | | vomiting | | |
| Rider ≫▶ | | wheezing | | |

ELECTRONIC MEDICAL RECORD CREATION AND RETRIEVAL SYSTEM

PRIORITY CLAIM

This application claims the benefit of priority from U.S. Provisional Application No. 61/248,741, filed Oct. 5, 2009, which is incorporated by reference in its entirety.

BACKGROUND OF THE INVENTION

1. Technical Field

This invention relates to an Electronic Medical Records system used to collect, store, retrieve, and analyze electronic medical data.

2. Related Art

Medical record keeping has developed over centuries of medical practice to provide an accurate account of a patient's medical history. Electronic medical records (EMR) are primarily intended for health care providers and refer to a set of databases that store the health information of patients including: diagnoses, treatments, lab results, drug allergies, and medical history. To access this patient note at a later time, a user will typically do a patient search and then open up a patient health history file which will show all past history. Some record keeping systems data mine out specific information like diagnoses, past medical history, and past surgical history and show them in a smaller version to ease the search for the provider but most systems still require the opening and closing of the electronic notes to search for the correct document.

The provider is not presented an easy method to add new symptoms, answers or diagnosis to the visit notes then the provider, as a result the visit notes look more like a cookie cutter view of the same data over and over again.

SUMMARY

An electronic medical records system includes a processor and a computer readable media. The computer readable media includes instructions stored in the computer readable media that are executable with the processor. The instructions in the computer readable media include instructions to prompt a user to select one of a selection view and an anatomical view, instructions to display a first list of pre-defined medical conditions in response to receipt of a view selection command indicative of a user selection of the selection view, instructions to retrieve and display an anatomical human image in response to the view selection command being indicative of selection of the anatomical view, and instructions to display a second list of pre-defined medical conditions for an area of the anatomical human image in response to an area command indicative of selection by the user of the area of the anatomical human image. The instructions in the computer readable media also include instructions to retrieve and display any one of a blue print template, a key questions list, or an interactive question series that correspond to one of the pre-defined medical conditions associated with either the selection view or the anatomical human image, and instructions to receive user entry of patient specific data into a selected one of the blue print template, the key questions list, or the interactive question series for a particular patient.

The electronic medical records system also includes instructions to prompt the user to select one of the blue print template, the key questions list, or the interactive question series as a vehicle to receive and store the patient specific data, instructions to display a first anatomical image representative of an external body surface view, a second anatomical image representative of an organ view, and a third anatomical image representative of a muscular skeletal view, and instructions responsive to user entry of the patient specific data to generate a predetermined sentence structure having one or more control variables, wherein the control variables comprise at least one of an automatic control variable populated by the system, a manual control variable populated in response to a user selection from a predetermined choice list of variables, and a semi-automatic control variable automatically populated by the system in response to receipt by the system of a manual user entry of patient specific data.

The electronic medical records system further includes instructions to construct a blue print created as a plurality of paragraphs of predetermined sentences populated with the patient specific data received via one of the blue print template, the key questions list, or the interactive question series, and instructions to display a key question and a choice list comprising a plurality of user selectable predetermined patient specific conditions that are each a possible answer to the key question.

Interesting features of the electronic medical records system include instructions to display an option list comprising a plurality of user selectable predetermined patient specific conditions that are also possible answers to the key question, instructions to receive a linking command indicative of a linking request received from the user to link the choice list and the option list within the blue print, and instructions to add one of the second plurality of user selectable predetermined patient specific conditions to the choice list in response to receipt of an add command indicative of an add request received from the user.

In another example, a method of creating electronic medical records includes displaying with a display device a first prompt to a user to select one of a selection view or an anatomical view of a human body, in response to receipt from a selection device of a view selection command representative of selection by the user of the selection view: retrieving from a database and displaying a list of pre-determined medical conditions, displaying with the display device a second prompt to the user to select one of the conditions from the list of pre-determined medical conditions, and in response to receipt from the selection device of a signal representative of selection by the user of a condition from the list of pre-determined medical conditions, retrieving a blue print that corresponds to the condition selected. The method also includes in response to receipt from the selection device of an anatomical view command representative of a user selection of the anatomical view: retrieving from the database and displaying an anatomical human image that includes selectable areas associated with a respective conditions list specific to a respective one of the selectable areas, in response to receipt from the selection device of an area command representative of a user selection of one of the selectable areas from the anatomical image and the condition from the respective condition list, retrieving the blue print that corresponds to the condition selected, and displaying with the display device a third prompt to the user to select one of a dynamic question series format, a key question format, or a blue print template entry format configured for entry of patient specific data into the blue print.

In still another example, an electronic medical records system includes a database that includes an images library comprising a plurality of anatomical human images, a blue print library comprising a plurality of blue prints each capable of containing patient specific data, and a data structure library comprising a hierarchical structure of categories comprising an evaluation type category, a human body system category, a chief complaint category and a list of pre-determined medical conditions. The electronic medical records system also includes a computer in communication with the database, the computer comprising a memory and a display, a selection view controller stored in the memory and executable by the computer to access the data structure library and the blue print library and to generate a selection screen for a particular patient on the display. The selection screen comprising an evaluation type indication, a human body system indication, a chief complaint indication and a medical condition associated with the chief complaint indication, the medical condition included in the pre-determined list of medical conditions and associated with a blue print containing patient specific data. The electronic medical records system further including an anatomy view controller stored in the memory and executable by the computer to generate an anatomy view for the particular patient, the anatomy view comprising an anatomical human image retrieved from the anatomical human images included in the database. The anatomical human image is divided into a plurality of predefined areas, and at least one of the predefined areas is associated with the medical condition and the blue print.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 5 is another example user interface screen of the electronic medical records system used to save blue prints using a selection view.

FIG. 9 depicts an example graphical user interface for launching a blue print using a human anatomical image.

FIG. 15 depicts an example graphical user interface for selecting a blue print from a selection view.

DETAILED DESCRIPTION OF THE PREFERRED EMBODIMENTS

Figure 1:
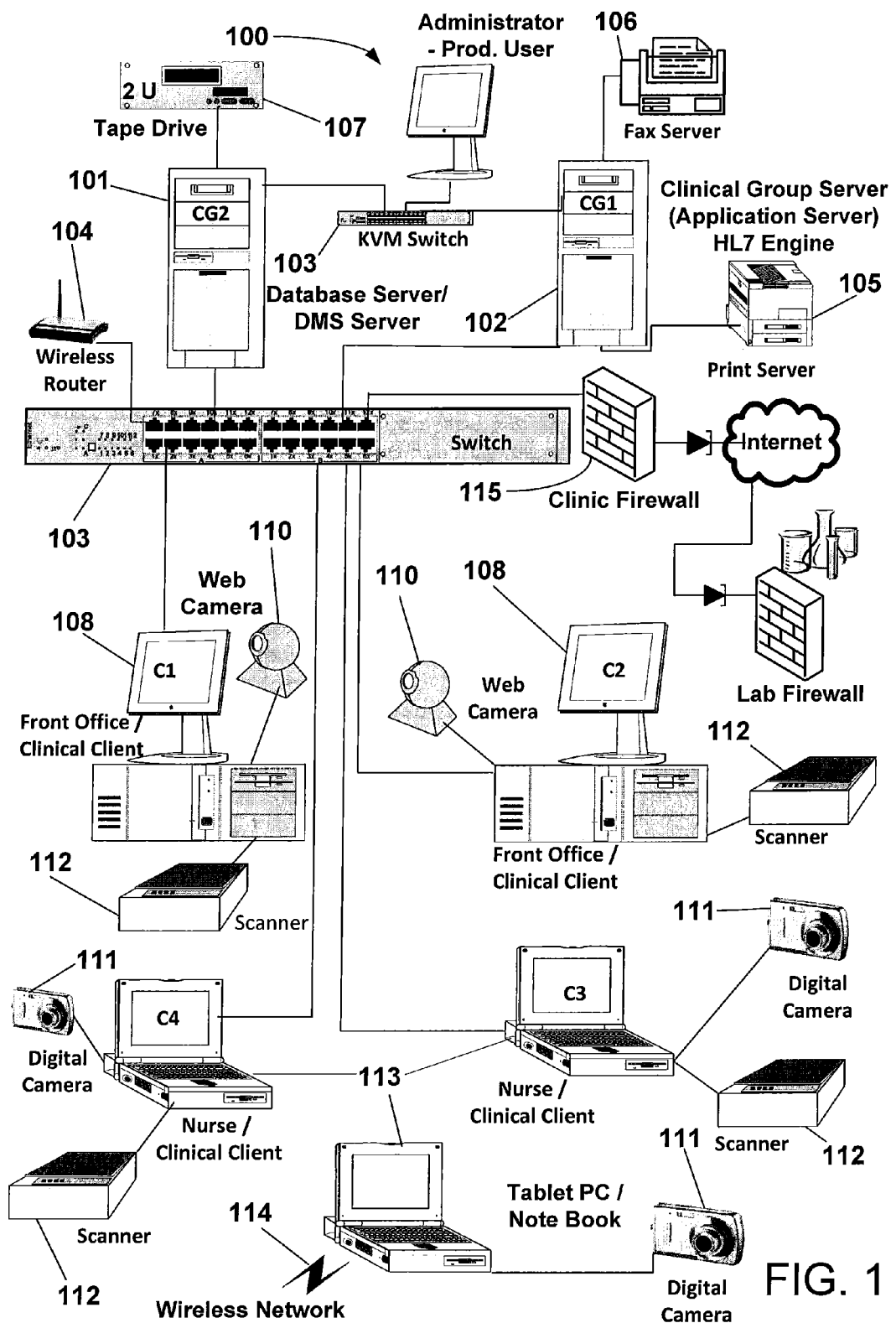
FIG. 1 is a block diagram example of an electronic medical records system that includes a blue print engine.

A key function of the presently described electronic medical records (EMR) system is to permit flexible creation, storage, and review of clinical data. As the volume of these data rise and individual patient records contain hundreds of documents, finding the areas of greatest interest becomes a challenge. EMR design choices such as the user interface to browse and select documents can simplify the search but the number of note titles may be quite large if more specific titles are used along with the sheer volume of chronic patient charts.

Designing a system that organically grows and integrates the use of anatomical images to create, store, and retrieval of medical data is a new method of interacting with a patient which then corresponds directly to an anatomical image in the electronic medical records system. The primary mechanism for creating a patient history is via interaction with the patient and accumulation of patient specific information medical documentation. Usually this occurs during interaction with the patient, such as during an office visit in which a user of the EMR system, such as a doctor, nurse, or other health care practitioner interviews the patient and collects patient specific information based on responses from the patient, observation of the patient and results of various patient related tests and/or measurements, which is then stored in the patient's medical record. The patient's medical record can be maintained in paper form, electronic form, or a combination of both and is typically created both during interaction with patient, and after interaction with the patient is completed. Systems that enable electronic medical record creation during an office visit primarily use a bottom up approach to medical documentation, which requires a diagnosis interpretation before beginning creation of a patient visit note. Using this method is often quite cumbersome, time consuming and labor intensive since more work is needed once questions are asked about the problem and symptoms because it takes the user time to first create a diagnosis of the issues by, for example, browsing through the different sections required to create a complete visit note, and then changing the diagnosis as more patient specific information becomes available.

In the presently described EMR system an anatomical image is used as part of a top down approach to patient interaction to create visit notes instead of selecting everything in textual form. This approach gives the user a better visual representation of all the different body systems including all the subsections of each system imbedded in each image. Not only is it an advantage to the user to have the ability to create and retrieve visit notes from an anatomical image, the EMR system also incorporates built in blue prints with each subsection of each system.

Blue prints can be pre-defined or manually built depending on the user preference and give the user another dimension to create notes. If the user does not want or need to use the image directly to create a complete visit note, they have the option to select a blue print(s) where they will have the option to use a created template, key questions, or question series modules. These three options will be created through a blue print module included with the EMR system. Templates will have the ability to use multiple fill in the blank options from categories including: option sets, duration, anatomy, tablet set, dictation, free type, etc. Key questions help a provider establish common ground with a list of questions that may be important to the general problem to help select a better diagnosis. Question series will show the most common questions that will be asked during a visit to help a user if needed. Examples of question series may include: Duration, condition state, associated symptoms, pain location, etc. When building these different types of options within the blue print module, the engine automatically converts plain text to variables and table sets with high, low, and unit of measurement on the fly.

Once a visit note has been created the user can then retrieve the past medical data by looking at a textual form health file or by directly at an anatomical image. The image will show reference points in form or dots directly on the image for the user to either hover over to view a transparent view of what and when a specific procedure or note was taken or they can select a specific section of a past visit note and include it in a new note they are starting to reference a past visit.

FIG. 1 is an example block diagram of an Electronic Medical Records (EMR) system 100 that includes representation of an embodiment of the blue print engine. The EMR system 100 illustrated in FIG. 1 is merely an example network deployment diagram which can be scaled up or scaled down depending on the type of clinic and its clinical process. In one example, the EMR system 100 may implement the blue print engine within one or more client server applications. In another example, the blue print engine can be deployed in one or more Applications as a Service, such as within an application service provider (ASP) model-Remote internet server (not shown). In the ASP model the Group server may be hosted in a central location where various clinics may connect to the Group server using Virtual private network (VPN).

In FIG. 1, as a client server application, a clinic may have a clinical group server and number of clinical clients connected over a network. The EMR system 100 may include one or more server computers comprising a database server 101, a clinical group server 102, and a plurality of client devices communicating over a network. The network may be formed to include one or more switches 103, wireless routers 104 and/or any network communication and routing devices capable of forming communication pathways.

The network may include the Internet, an intranet, an extranet, or any other form of communication backbone that provides a communication framework between computing devices. Communication within the network may be performed with a communication medium that includes wireline-based communication systems and/or wireless-based communication systems. The communication medium may be, for example, a communication channel, radio waves, microwave, wire transmissions, fiber optic transmissions, or any other communication medium capable of transmitting data, audio, and/or video information. Communication over the network may be implemented in any communication language or protocol, such as a packet based protocol. In one example, the EMR system may include a clinical network formed as an intranet that includes a firewall and connectivity to other networks, such as the internet, which are outside the firewall of the clinical network.

The servers may be any form of computing device(s) capable of receiving requests and transmitting responses over the network. In addition, the servers may be capable of performing the functionality hereinafter described. The servers may include a network interface, a processor, a user interface, and a memory. The network interface is coupled with the network and may be any combination of hardware and software that interfaces with, and enables communication over the network. For example, the network interface may be a NIC card operable with TCP/IP, or a modem. The processor may be any device(s) or mechanism(s) capable of executing instructions, receiving inputs, and generating outputs, such as a central processing unit (CPU). The processor may direct the operation and provide the overall functionality of the server. The processor is coupled with the network interface and may transmit and receive communication over the network. As used herein, the term "coupled," "connected," or "interconnected" may mean electrically coupled, optically coupled, wirelessly coupled, and/or any other form of association providing an interface between systems, devices, and/or components.

The user interface may include any visual, audible and/or tactile mechanism that allows a user to provide and receive information from the EMR system 100. The user interface may include a display, such as a graphical user interface (GUI), and an input device, such as a keyboard, touch screen, or microphone. In addition, the user interface may include a pointing device, such as a mouse or stylus, and/or any other device(s) or mechanism(s) that provide a user with the capability to provide to the processor and/or receive from the processor information and/or commands.

The memory may be one or more information storage devices accessible with the processor. The memory may be at least one magnetic data storage device, such as a hard drive, an optical disk, a magnetic tape, etc., and/or at least one electronic memory device such as flash memory, random access memory (RAM), or any other mechanism or device capable of storing electronic data. The memory may be located within the servers. Alternatively, the memory may be located anywhere that allows communication with the servers over the network. In another alternative, a portion of the memory may be located within the servers, and other portion(s) of the memory may be located elsewhere within the network.

The memory may include applications, databases, and data. The database may be a single database or multiple databases. The databases may include an images library that stores a plurality of anatomical human images, a blue print library that stores a plurality of blue prints each capable of containing patient specific data, and a data structure library comprising a hierarchical structure of categories comprising an evaluation type category, a human body system category, a chief complaint category and a list of pre-determined medical conditions.

The applications may include an operating system to provide the operational functionality of the computing device, communication applications, database related applications, one or more applications providing the functionality of the EMR system as herein described, and any other software and/or firmware programs to provide the functionality described herein. The applications may be stored in the memory in the form of instructions that are executable with the processor. The memory may also store patient information in the form of one or more patient records for each patient, patient related images, patient specific blue print information, security related information, and any other data used by the EMR system as described herein. In addition, user interface screens, user profile data, and/or any other data related to the functionality of the EMR system may be stored in the memory.

The clinical clients may include any type of desktop personal computers, notebooks, tablet personal computers, personnel digital assistants (PDA), mobile telephones, and/or any other form of computing devices capable of being connected in the network. The clinical clients may include a processor, memory and a user interface in any form, as previously discussed. The clinical clients may operate as standalone computing devices in communication with the servers, terminals in communication with the servers, or any other form of interfacing with the servers to provide for two way communication of data. In one example, the clinical clients may include an application operating as portal, or browser into which information is populated from the servers and user entries are received and transmitted to the servers.

In FIG. 1, the database server 101 may be a database server and document management server (DMS) which can host a database system and a document management system. The database may be any form of data repository system, such as a Relational Database Management System (RDBMS), an object-oriented database, an extensible markup language (XML) database, a file system, memory structures, or other now known or later developed data organization and storage mechanism. The document management server may store all the clinical documents in any form of data repository system as previously discussed. The database server and the document manager server 102 may be accessible to the users via a user interface, or over the network, using a portal, such as a web browser. In addition, the data contained in the database server 101 may be accessible over the network by users and/or applications.

Clinical group server 102 can act as application server, document management server, database server and/or interoperability server. The clinical group server 102 can be deployed on one single server as logical layers or multiple servers. The clinical group server 102 includes an application server which will interact with the database server and clinical client requests. The application server may host the application services and interact with different systems, such as a print server 105 and a fax server 106. The application services hosted on the application server may interact with third party components and external services, such as HL7 systems. Clinical business rules and work flows may be developed and operated within application services. The application server can be configured to only honor requests received from user that have a predetermined level of permission, such as permission to connect to the application services.

Each of the services in the EMR system 100 may be secured with any form of security and authentication systems. For example, some or all of the EMR system 100 may employ an encrypted username and password for authentication such that only authorized users may be permitted to access the EMR system 100. In addition, various levels of security may be established such that at least some of the authorized users are provided with less than full access to the EMR system.

The EMR system 100 may also include data storage capability in the form of a back up mechanism capable of backing up specified data in a secondary data storage. The secondary storage of backup data may be completed using a predetermined schedule, such as once per day. In FIG. 1, the backup mechanism 107 is a tape drive, however, in other examples, any other memory storage device may be used to perform the backup function. The EMR system 100 may also include an audit log configured to capture data for every point of access to the EMR system 100. The audit log may be maintained for every activity on the servers.

The switch 103 may be a router/switch, which enables devices connected to the network, such as the clinical network, to communicate. The wireless router 104 may be a wireless router configured and connected to the network, such as the clinical network, which enables the clinical clients (desktops, notebooks, tablet pc, and/or PDA) to connect to the network without a cable. The print server 105 is a print server which may be connected to the application server, or any other device providing access to the network in order to serve the requests sent by different clients to print documents from applications. The application services hosted to communicate and print the documents with the print server may serve the client. A printer log may be maintained in the clinical group server 102. The fax server 106 is fax server which may be connected to the application server, or any other device providing access to the network in order to provide receipt of incoming faxes and sending of out going faxes from the applications. All incoming faxes may be stored and uploaded to the document management system to allow for later retrieval of faxes.

The client devices may include a plurality of clinical computers 108 which are connected to the network, such as the clinical network, in order to host client applications. The clinical computers 108 may authenticate and authorize the user to access the application services hosted on the clinical group server 102. The clinical computers 108 may be front office/clinical client and may include a processor, memory and a user interface, as previously discussed.

One or more peripheral devices may be coupled with the clinical computers 108. Peripheral devices may include, for example, a webcam 110, a camera 111, a scanner 112 or any other device external to the personal computers 108, which may be used to extend the functionality and operability of the EMR system 100. In one example, the scanner 112 may be coupled to one of the clinical computers 108 in order to allow scanning of paper documents for storage and use within the EMR system 100. Applications within the EMR system may convert the scan data collected to image documents for storage on the document management system using the application services. The webcam 110 may be coupled with the clinical computer 108 in order to allow a user to capture moving digital images for storage in the EMR system 100, to enable live communication, such as in a teleconference, to allow remote observation, or for any other application related to user patient interaction. For example, a user may take video pictures of patients and store them on the document management system using the application services. Similarly, the camera 111 may be used to capture still images, such as to take pictures of a patient and store them on the document management system using the application services.

FIG. 1 also includes a wireless computing device 113, such as a wireless connected tablet pc, to communicate with the application server. In one example, the wireless computing device 113 may use a client application to communicate with the application server. Communication may be over a wireless network 114 using the wireless router 104. Alternatively, or in addition, the wireless computing devices 113 may be wireline connected into the EMR system 100.

The basic layout of an example of Electronic Medical record visit notes output is a blue print containing one or more paragraphs. Each of the paragraph can be made up of one or more predetermined sentences with a predetermined sentence structure having predetermined fixed, non-changing text. Each sentence can include one or more fillable data locations configured to receive one or more control variables. The control variables may be selectively inserted by the EMR system 100 between the fixed non-changing text included in the sentence. An example output of an electronic medical record visit note in the form of a blue print is:

"The patient complains of claudication and difficulty swallowing. He has associated symptoms/conditions of dizziness, orthopnea and palpitation."

"He denies sweating and swelling of the feet. The symptom(s) started 2 weeks ago."

In this example, the underlined text represents the control variables that are selectively inserted by the EMR system based on information gathered during the patient visit. The control variables in this example include:

1. claudication and difficulty swallowing (symptom/condition description)
2. He (patient specific identifier, such as gender)
3. dizziness, orthopnea and palpitation (symptom/condition description)
4. sweating and swelling of the feet (absent symptom/condition description)
5. 2 weeks ago. (start of symptoms/conditions)

Each control variable can be filled in at runtime either automatically by the EMR system or by direct or indirect selection by a user of a control variable. Each of the control variables describes user controlled parameters descriptive of a patient and/or one or more of the patient's medical conditions. Medical conditions include one or more symptoms of the patient, such as feverish or dizzy, and/or one or more diseases of the patient, such as flu or diabetes. The user control variables may be responsive to user entry of the patient specific data via a user interface. As described later, entry of patient specific data may include selection of choices presented to the user, direct entry of patient specific data, user interaction with one or more key questions lists and/or user interaction with one or more interactive question series.

In one example, there can be three types of control variables, namely: 1) Automatic control variables, 2) Manual control variables and 3) Semi Automatic control variables. Automatic control variables are the patient specific variables that are automatically filled by the EMR system based on the context of a particular patient. For example, the variable automatically filled with the patient identifier "He" by the EMR system 100, which, in this example is attached to the gender of the patient. In one example, if the patient is male the system will replace the blank with "He," whereas if the patient is female the system will substitute the blank with the term "She." Alternatively, other patient identifiers, such as the patient's first name, family name, identification number, or any other patient specific identifier may be used.

Manual control variables are the variables that are filled by the user using an interface. For example, the interface may include a choice list of predetermined choices selectable by the user. In the previously discussed example paragraph, the terms "claudication" and "difficulty swallowing" may be manually selected from a choice list. In one example, the choice list may contain user selectable predetermined choices such as:
 claudication
 difficulty swallowing
 dizziness
 orthopnea
 palpitation
 sweating
 swelling of the feet The user may select one or more of the choices in the choices list that apply to a question, such as in the above paragraph were claudication and difficulty swallowing were manually selected. Generation of questions as part of a patient encounter is described later.

Semi Automatic controls are variables that are populated by underlying logic based on a current action of the user. For example, if there are two complimentary questions such as
 1. Patient complaints of _____; and
 2. Patient denies _____

If, for example, there are a total of seven common complaint choices listed in a choice list associated with a semi-automatic control, and among them the patient complains of two choices as answers to the first of the two complimentary question, the remaining common five complaint choices may be automatically selected as answers for the second complimentary question by the EMR system 100. In other examples, any number of complimentary questions may be associated with logic to form semi-automatic controls.

Figure 2:
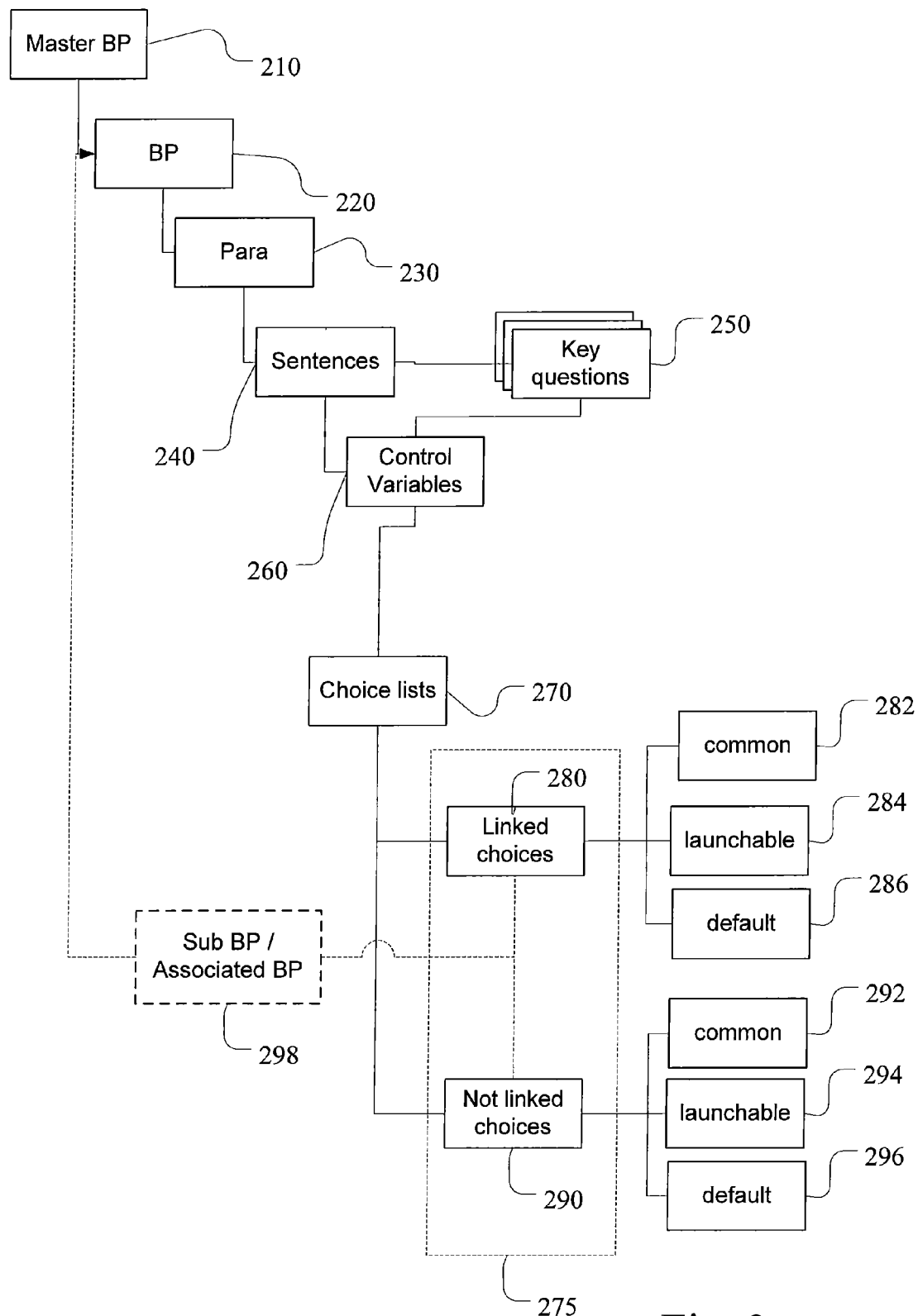
FIG. 2 is an example block diagram illustrating the functionality of the blue print engine within the electronic medical records system.

FIG. 2 is an example of a blue print engine 200 within the EMR system that is representative of a blue print element hierarchy within a blue print module. The blue print (BP) engine 200 is a functionality and a data structure that contains many elements. A master BP 210 is a collection of blue prints 220. As used herein, the term "blue print" describes one or more electronic patient specific data records in the form of paragraphs populated with predetermined fixed text and control variables. Each of the BP's 220 may contain one or more paragraphs 230 that are made up of sentences 240. Each sentence 240 can be made up of one or more key questions 250. Each sentence 240 can also include one or more control variables 260. Each control variable 260 may have one or more key questions associated with it. For example, in the sentence "The patient complains of claudication and difficulty swallowing." The following are different attributes of the above sentence:
 Predetermined fixed non-changing text sentence: "The patient complains of _____."
 Key question: "Patient's complaint?"
 Answer control variables choice list (Within a subsystem called CVS Cardio Vascular System Symptoms, as discussed later.)
Choices:
 claudication
 difficulty swallowing
 dizziness
 orthopnea
 palpitation
 sweating
 swelling of the feet In addition to showing an example of the BP (blue print) element hierarchy, FIG. 2 also describes an example of how the blue prints may be created with different elements and how they may be organized in the blue print. Master blue prints 220 are a collection of individual blue prints. One or many blue prints 220 may be grouped together to form a master blue print. Each blue print 220 can have one more sub blue prints 298. The sub blue prints 298 may be associated to a choice in linked choice 280 or unlinked choice 290, to describe the choice even further.

For example, assume that we have "Diarrhea master BP" and have a collection of the following blue prints 220:
 1. Causes BP
 2. Risk factor BP
 3. Symptoms BP
 4. Diagnosis BP
 5. Treatment BP Blue prints are created with the collection of paragraphs 230, as previously discussed. If, for example, "Causes BP" includes two paragraphs, and "Causes BP" is selected, the corresponding example blue print 220 may be created and displayed as:

Paragraph 1

Causes may include: Food intolerance, medications, irritable bowel syndrome. The patient has chronic diseases liver disease, diabetes, and hyperthyroidism.

Paragraph 2

Patient has infections with the food poisoning, bacterial, viral, parasitic, and fungal. Diarrhea is caused by using the medications like antibiotics, magnesium-containing antacids, high blood pressure medications, quinine, cancer chemotherapy and Laxatives.

Each paragraph 230 is made of one or many sentences, 240, as previously discussed. In the previously discussed example, each paragraph 230 is created with two sentences:

Paragraph –1, sentence –1 Causes may include: Food intolerance, medications, irritable bowel syndrome. Paragraph –1, sentence –2 The patient has chronic diseases liver disease, diabetes, and hyperthyroidism.

Paragraph –2, sentence –1 Patient has infections with the food poisoning, bacterial, viral, parasitic, and fungal. Paragraph –2, sentence –2 Diarrhea is caused by using the medications like antibiotics, magnesium-containing antacids, high blood pressure medications, quinine, cancer chemotherapy and Laxatives.

Each sentence 240 is created with one or more finable data locations for one or more control variables 260 interspersed, or disposed, in and around predetermined fixed text, as previously discussed. Each sentence 240 may be associated with one or more key questions 250.

Paragraph –, sentence –1 Causes may include: {paragraph –1, sentence –1, control variables set-1} Food intolerance, medications, irritable bowel syndrome. Paragraph –1, sentence –2 The patient has chronic diseases such as {paragraph –1, sentence –2, control variables set-2} liver disease, diabetes, and hyperthyroidism.

Paragraph –2, sentence –1 Patient has infections with the {paragraph –2, sentence –1, control variables set-1} food poisoning, bacterial, viral, parasitic, and fungal. Paragraph –2, sentence –2 Diarrhea is caused by using the medications like {paragraph –2, sentence –2, control variables set-2} antibiotics, magnesium-containing antacids, high blood pressure medications, quinine, cancer chemotherapy, Laxatives.

Key questions 250 may be associated with the respective sentences 240, for example:

{Key question –1} What are diarrhea causes?

Paragraph –1, sentence –1 Causes may include: {paragraph –1, sentence –1, control variables set-1} Food intolerance, medications, irritable bowel syndrome.

Each control variables set can be a collection of control variables 260 contained in a choice list 270. Choice lists 270 can include control variables 260 that are each characterized with a choice type 275. In FIG. 2, the choice types 275 include control variables characterized as linked choices 280, and/or control variables characterized as unlinked choices 290.

In one example, using the previously discussed Paragraph 2 first sentence, first control variable set, the choice list may be depicted as:

Paragraph –2, sentence –1 Patient has infections with the {paragraph –2, sentence –1, control variables set-1}

Choice list: food poisoning, bacterial, viral, parasitic, and fungal.

Each of the control parameters in control variables set-1 of the choice list 270 that are identified as linked choices 280 may be further indicated as common characteristics 282, and/or launchable characteristics 284, and/or default characteristics 286. Accordingly, Paragraph –2, sentence –1 Patient has infections with the {paragraph –2, sentence –1, control variables set-1} may include control parameters in the choice list 270 that are linked choices 280 indicated as:

Choice List:

food poisoning {common, launchable, default} bacterial {common} viral parasitic fungal

As described in FIG. 2, blue print may include a collection of paragraphs. Each paragraph is a collection of one or more sentences. Now we are going to detail out the functionality of sentence creation within the EMR system 100.

Figure 3:
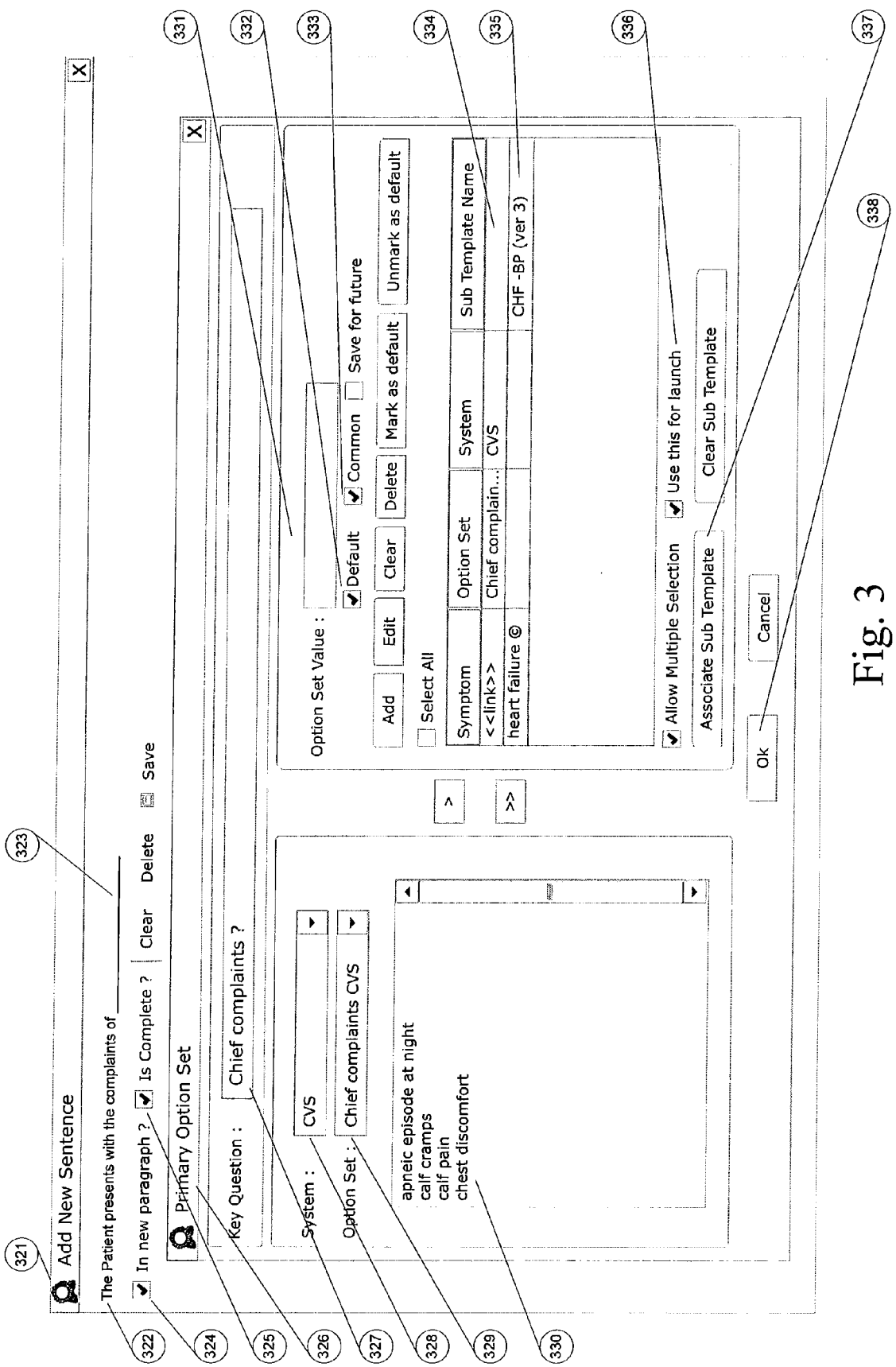
FIG. 3 is an example user interface screen of the electronic medical records system used in blue print creation.

FIG. 3 is an example user interface screen 321 of the EMR system 100. In FIG. 3, the user may click on an "add new sentence" button or otherwise instruct the EMR system 100 to generate the graphical user interface illustrated in FIG. 3. In other examples, any other form of interface may be generated that includes similar functionality. The interface enables a user to manually add a new sentence and/or paragraph to a blue print. For example a user can add a sentence to a blue print such as:

"The patient presents with the complaints of heart failure."

If we match to the sentence definition described in FIG. 2, the above sentence includes a predefined fixed text sentence 322—"The patient presents with the complaints of." The control variable {heart failure} may be made part of a control variables set, which holds a collection of control variables in a choice list.

The user can, for example, review the sentence and manually add the control variable into the fillable field 323 by selection from a choice list. If the sentence being added to the blue print is a new paragraph (as a first sentence), a user may select a new paragraph selector 324 as shown in the FIG. 3. The user has two options: 1) continue with the current sentence, which would mean the current sentence is not complete, or 2) select a sentence complete selector 325 when the added sentence is complete.

The control variable {heart failure} is a control variable that may be included in a control set 326. In FIG. 3, the control set 326 is a "Primary Option Set." The EMR system may include a defined list of control sets that change values. The primary option control set 326 may be selected by a user to complete the sentence.

Each sentence may also be associated with a key question 327. In one example, the user may enter a key question in a key question field 327 for association with the sentence. The user may also add a list of choices to the control set 326 available for selection of the fillable field 323. The EMR system also provides the capability to select a linked set. The linked sets may include a system 328 selected with a system linked set selection, and an option set 329 selected with an option linked set selection. Each linked set may be formed with a hierarchy. Each human body system or a set of choice lists can be grouped together under a system 328 or a super set that can be selected from the system link set selection. Within each system 328 or super set are one or more option sets 329 each containing choice list names; that are selectable by a user from the option link selector set. For example, Cardiovascular system CVS" is the system 328 {super set} selectable with the system linked set selection, and "Chief Complaints CVS" is the option set 329 selectable from the option linked set selection. When the user selects a particular option set 329, the EMR system and/or BP engine may retrieve and list a predetermined list of choices of control variables associated with the selected option set 329 in a choice list 330.

The user can select individual control variables, or medical conditions, from the choice list 330, or the user can set up a link to the control set 326. When the user establishes a link between the control set 326, which is selected as "primary option set" in FIG. 3, and the system 328, the option set 329 may be grown organically as users use the EMR system. As discussed later, organic growth of the EMR system may be based on users updating and refining the blue prints. Since the blue prints are stored centrally and are retrieved as a link to a control variable, user selection of a blue print via a linked control variable results in the EMR system retrieving a latest version of the blue print associated with the control variable, even if the blue print has been changed since the association, or link, between the control variable and the blue print was established. For example, more control variables may have been associated with the blue print and now appear as possible entries in the fill-able fields of the blue print. At any point of instance when a new control variable is added to the choice list for an option set 328, a link is created such that the new control variable added to the choice list is remembered as being associated with the option set 329 and the control set 326 such that the current data is populated to the end user For example, if a selected option set 329 is associated with twenty-five control variables in the choice list, and a user adds to the option set definitions of another fifteen control variables, when the link is established the EMR system presents forty control variables in the choice list to the end user.

Control variables may be added to the choice list by user entry of an option set value 331 in an option set value entry field. For example, a user can enter a choice name in a text box. Each control variable in the choice list can be characterized as default, common and uncommon characteristics, as previously discussed. In the example of FIG. 3, we are adding "heart failure" as a control variable in the choice list with the following characteristics: common and default by selection of a default indicator 332 and a common indicator 333. A User has an option to select any of the characteristics for the choice before adding to the option set. A choice can be associated with a sub template (which is also referred to as a sub blue print) using choice selection that includes a first choice association field 334 and a second choice association field 335. In FIG. 3, the second choice association field entry 335 includes the choice Heartfailure, which is associated with a sub template identified as CHF BP (ver 3), to allow description of heart failure in detail within the sub template. The first choice association field 334 can be left blank when a choice need not be associated with a sub template. As described later, the choice(s) indicated in the choice selection will be shown in as choice(s) 957 for launching the template in the template usage area of FIG. 9 when checkbox 336 "Use this for launch" is checked.

Each of the choice lists can be associated with a sub blue print, which is a collection of one or more paragraphs. For example, a user may elect to associate the control variable "heart failure" with a heart failure detail sub blue print by selection of an associate sub template selector 337. The control variables in the selected set of choices or link set can be used to launch a corresponding blue print by selection of a use for launch selection 336. Those control variables that have been selected as use for launch are populated to the user when the user clicks on the control variables in the choice list. A user may click on or otherwise select an "Ok" selection button 338, once the sentence creation is completed.

Figure 4:
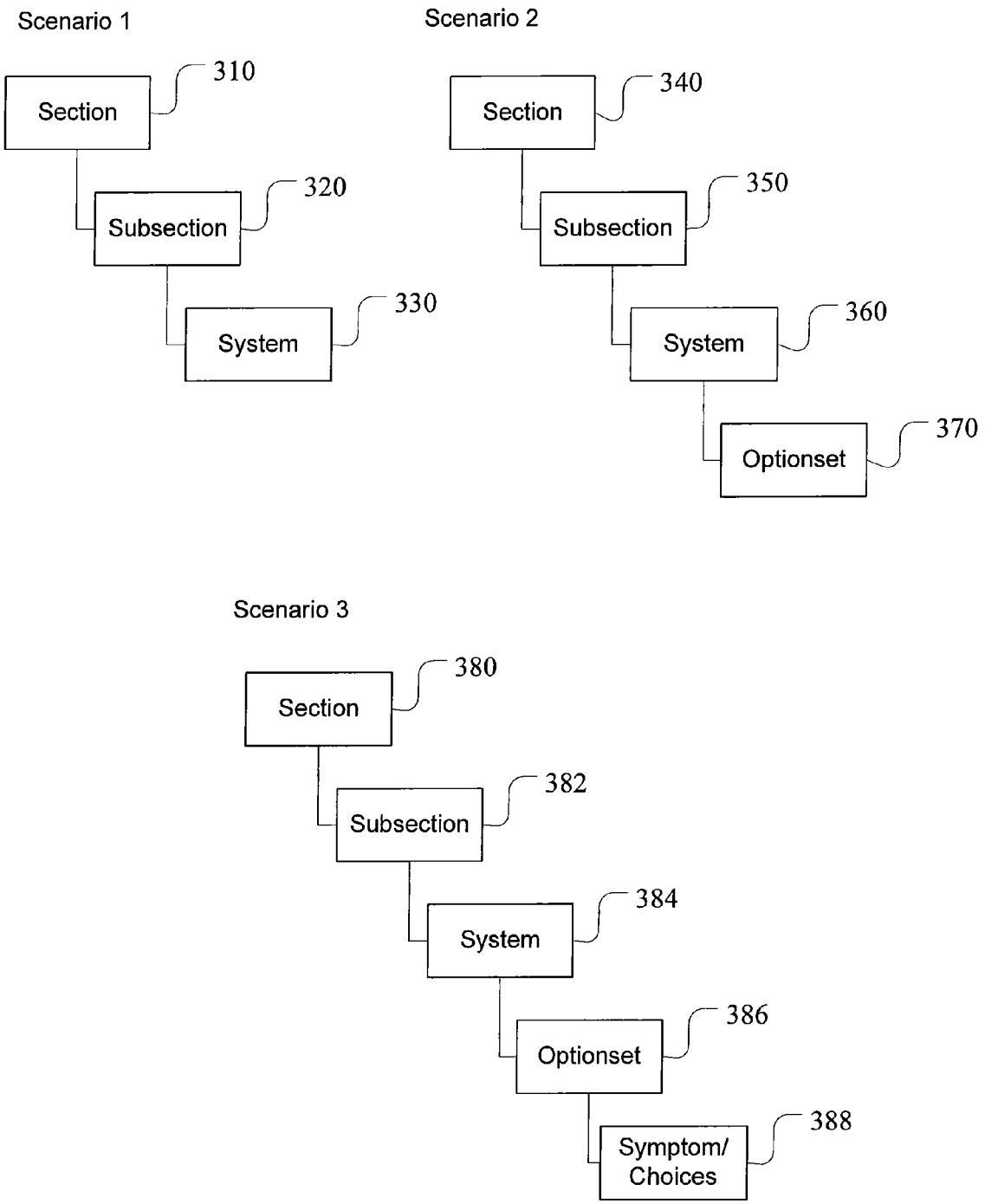
FIG. 4 represents various examples of the hierarchal organization of a blue print in the EMR system.

FIG. 4 represents various examples of the hierarchal organization of a blue print in the EMR. Each section 410, 440, 480 in EMR may have a collection of one or more sub sections 420, 450, 482. Each section 410, 440, 480 may be top level hierarchy in the EMR. For example taking "Subjective" as a section, CC & HPI (Chief complaint & History of present Illness), PMH (Past Medical History), and/or PSH (Past Surgical History) may be sub sections 420, 450, 482 that are grouped and assigned to that section 410, 440, 480. Thus:
Subjective—section 480
CC & HPI subsection 482
PMH—subsection 482
PSH—subsection 482

Each subsection 420, 450, 482 may include one or more of a set of systems 430, 470, 484. For example, CVS (Cardio Vascular System) may be a system 430, 460, 484. Each of the systems 430, 470, 484 may include one or more option sets 470, 486. Option sets 470, 476 may include one or more of a set of control variables that are medical conditions or symptoms/choices included as a choice list 488. Thus, for example:
Subjective 480
  CC & HPI 482
    CVS 484
      Chief complaints 486
        Heart failure 488
        Chest pain 488
        Chest congestion 488

In this example, the subjective section 480 includes CC & HPI sub section 482, CC & HPI sub section 482 includes CVS system 484, CVS system 484 includes Chief Complaints option set 486, and Chief complaints option set includes an options list that includes the control variables Heart failure, Chest pain and Chest congestion as symptom/choices 488. As described by the hierarchy in FIG. 4, we will now see how that is represented in the interface.

Figure 5:
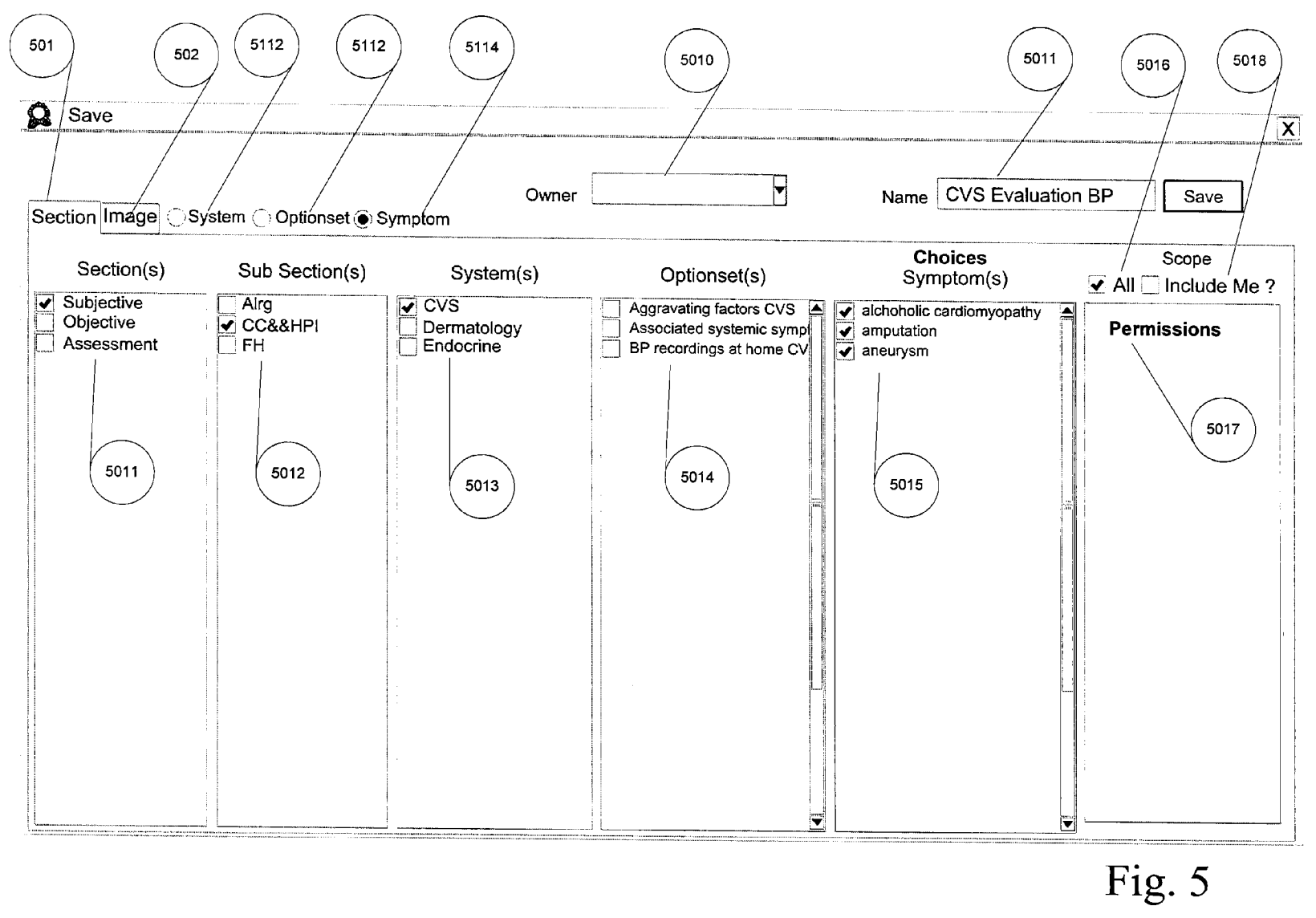

FIG. 5 is an example user interface screen used to save blue prints that have been created. In other examples, other user interface screens may be used that provide similar functionality. When a user creates sentences and paragraphs, as previously discussed, and is ready to save the blue print, the user may select a save function, such as by clicking a save button to bring up a user interface, such as the user interface depicted in FIG. 5.

In the example of FIG. 5, the user can save the blue print in two ways using either a section mapping 501 or an image mapping 502. Image mapping 502 provides image based saving and will show an image, such as an image of a human body, to a user. As described in detail later, the user can draw a marking on the image of the human body, and save the blue print in association with the marking. The section mapping 501 provides for section based saving of blue prints in which blue prints may be saved by association of a blue print with the hierarchical organization within the EMR system.

In the case where a user selects section mapping 501 for saving the blue print, all the sections 480 (FIG. 4) in the EMR system may be displayed in a section selector 5011 to the user in order for the user to select which one of sections the blue prints are to be saved in association with. When user selects any one or more of the sections, the system will populate a sub sections selection 5012 with a list of available sub sections 482 (FIG. 4) mapped to the selected sections. The user has option to select multiple sections or a single section. When the user selects multiple sections, the EMR system will list all the sub sections mapped to the respective selected systems in the subsection section 5012.

Then user may then select one or more subsections from the subsection section 5012. In response, the EMR system will bring all the systems 460 (FIG. 4) that are associated with the selected subsections into a system section 5013. The user has option to select multiple systems or a single system. When user selects one or more systems, the interface will list of all option sets 470 (FIG. 4) in an options sets section 5014. The user can select one or more option sets and the EMR system will retrieve and show the control variables associated the selected option sets in the form of a choice list in a symptoms section 5015. The control variables contained in the choice list that are displayed to the user in the symptoms section 5015 may include control variables having common characteristics, default characteristics and uncommon characteristics. Thus, the user may save a blue print in association with at least one level of a hierarchical structure. The levels of the hierarchal structure may include a description of a type of evaluation performed by the user to develop the blue print, a system of the human body to which the blue print pertains, a chief or main complaint of the patient during the office visit that precipitated creation of the patient specific blue print, and a list of predetermined medical symptoms which are selectable by the user to describe the patients current medical condition.

A user can set permissions for a list of system users in a permission section 5017. Once a user is set to have permission, the user may access the blue print. Although not illustrated in FIG. 5, the EMR system may show a list of all the active users of the EMR system in which each user is individually selectable to have permission to access the blue print. The permission section 5017 may also include an all selector option 5016 to select all the users to have permission to access the blue print, or an include me selector option 5018 such that the user has the option to set the permission/scope for himself only; and all other users are deselected in the scope list included in the permission section 5017.

In FIG. 5, the user can also select an owner for the blue print with an owner selection 5010. The owner selection 5010 may include a selectable list of users in the system. Once a user is selected as the owner of a blue print, only the owner has permissions to edit/delete the blue print definition. A user can give a name to the blue print using a name selection 5011 and select to save the blue print under the given name using a save selector, such as by clicking on a save button.

When the user has selected during the sentence creation any of the control variables included in the control set as a launcher, as previously discussed with respect to FIG. 2, in this interface the EMR will remember the system, option set, symptoms/choice list and automatically selects to the end user when the user selects the subsection. The launcher includes a choice list that is used to open the blue print. Usually the answers (choices) to the first question in a blue print will be marked as a launcher. For example, in a Cardio vascular blue print, the first question may be "What is patient's complaint?" Possible Answers may include: chest pain, shortness of breath, swelling, etc. The user could search and open the Cardio vascular blue print manually. Alternatively, the user can open the blue prints, such as the cardio vascular blue print by hovering the mouse over an image, such as the heart image. The heart image 955 is identified as being part of the Cardiovascular (CVS) system. The choices are identified as being within the CVS system. On mouse hover the EMR searches for all the blue prints that have launcher answers corresponding to the heart image. The system then presents the choices 957 to the user. If the same answer, such as for example, "chest pain" is present in more than one blue print, then the EMR system may present another screen with a list of blue prints that has this choice as an answer. Once the user selects the blue print name, the EMR opens a blue print, such as the blue print example of FIG. 11, and automatically marks the chest pain selected 1118 as the first answer.

In FIG. 5, a user can save the blue print in any of three modes: System mode 5112, Option set mode 5113, Symptom mode 5114. When the blue print is saved with system mode 5112, a blue print can be launched with all the options set and its symptoms/choice list. For example, we will consider three blue prints, namely: General Cardio blue print (BP), Bypass surgery blue print (BP) and Chest pain blue print (BP).

1. General cardio BP may include a launcher question of what is the problem? The answer choices could be all possible cardio symptoms such as chest pain, shortness of breath, swelling, etc. The general cardio BP is saved with system mode 5112.

2. Bypass surgery BP may include a launcher question of what is the problem? The answer choices could be a determined number of symptoms. For example, the answer choices could be two symptoms such as chest pain and shortness of breath. The bypass surgery BP is saved with option set mode 5113, 3. Chest pain BP may include a launcher question of what is the problem? The answer could be chest pain. In this example, only one answer is available since it is a specialized template for Chest pain. The chest pain BP is saved with symptom mode 5114, When the user hovers the mouse over an image, such as a heart image, the EMR system may search the BP's that are associated with the heart image and retrieve the associated BPs. For example, the system may get the three previously discussed BPs. Next, the EMR may find a first question of each BP and consolidates the answers. For example, the user may see chest pain, shortness of breath, and swelling as answers. When the user selects one of the answers, such as swelling, the corresponding BP, such as the Cardio BP, may be opened automatically as it is the only BP that has that answer. When the user clicks an answer present in multiple BPs, such as chest pain which appears as an answer in all three of the BPs, the screen may the user to select one of the three BPs.

When a new answer that is not found in the list needs to be added, for example, chest discomfort, the EMR system will add the choice to the appropriate group, so that hovering the mouse over the corresponding image, such as the heart image, brings up chest discomfort and opens the corresponding BP, such as the General Cardio BP, but does not open Chest pain BP.

In summary when option sets are added organically during operation of the EMR system, the corresponding blue print is automatically associated with the newly added option sets. When the blue print is saved with option set mode 5113, the blue print can be launched with all the symptoms/choice list. When the symptoms are added organically during operation of EMR system, the blue print may be automatically associated with those newly added symptoms. When the blue print is saved with the symptom level mode 5114, the blue print may be launched only with the symptoms selected for the launching.

Figure 6:
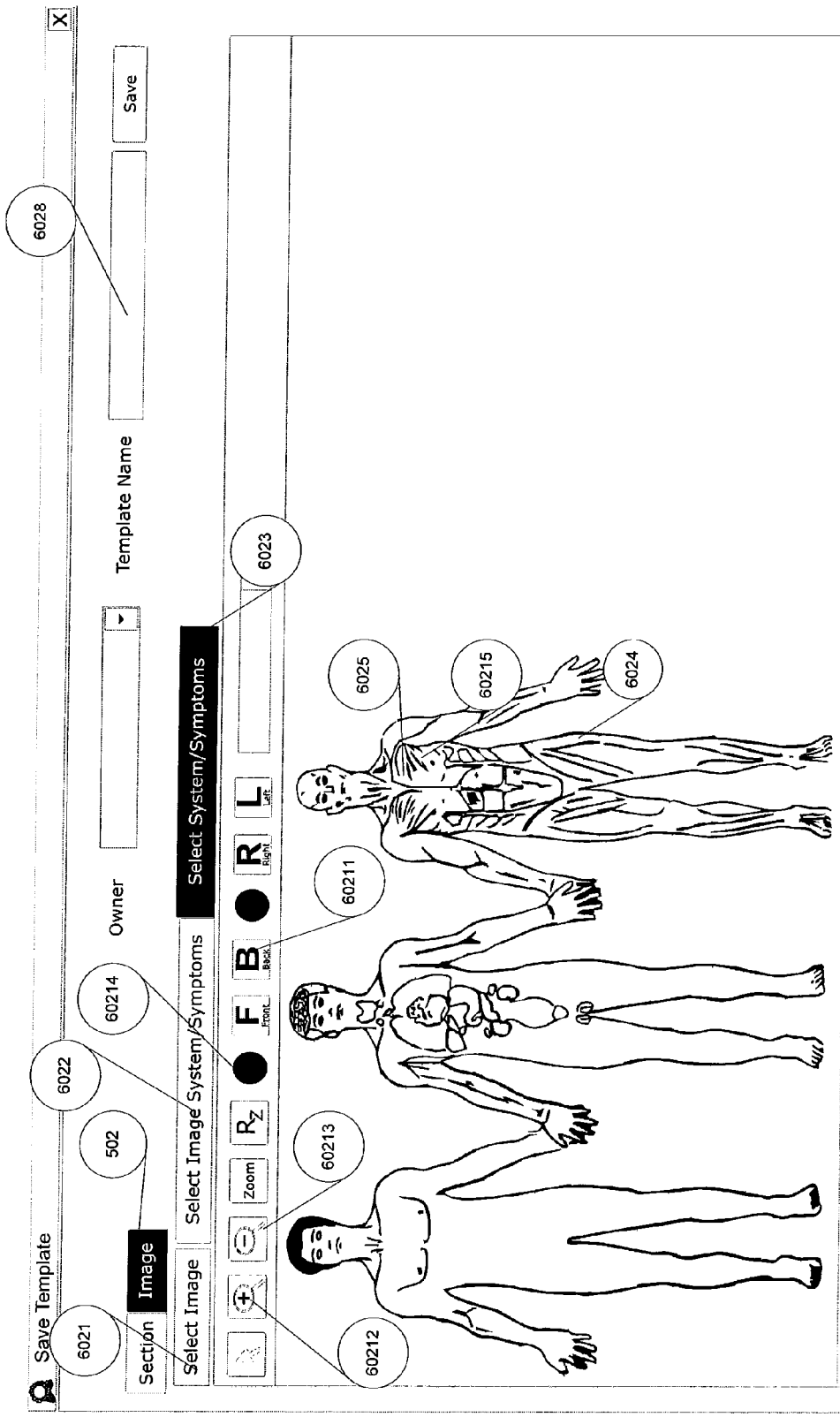
FIG. 6 is another example user interface screen of the electronic medical records system used to save blue prints using an anatomical image view.

FIG. 6 is an example of a graphical user interface for the image mapping 502. Image mapping 502 represents an alternate method to save the blue print using an image, such as a human body. Since the images and systems are interconnected within the EMR system (see FIG. 7), a blue print saved in one method e.g. System mapping 501 can be retrieved using another method e.g. Image mapping 502, and vice versa.

The example user interface depicted in FIG. 6 shows three options to save the blue print using image mapping 502. Within the EMR system, users can select an image from a list of configured images stored in an image library using an image selector 6021. Once selected and displayed, a user may manipulate the retrieved images by selection of an image orientation selector 60211 that provides the capability to manipulate display of an images such as to change the orientation of the image to front, left, back, or right. A user may also use an image zooming selector 60212 to increase magnification of an image, and an image un-zooming selector 60213 to decrease magnification of an image. A user may also select a default image selector 60214 such that when the user is in orientation mode, the user can go back to the original image selected mode. The user may also use a marked body mapping selection 60215 to mark a location of the image in order to associate a blue print with the marked area of the image.

Any form of image related to medical care of a patient may be stored in the EMR system. For example, images can be specific and detailed for a specialist, such as an image of a heart that includes valves and other details for a cardiologist, or images can be relatively generic for family practice, such as the combination of three images depicted in FIG. 6.

In FIG. 6, the example images depicted include a skin system 6035, an organ system 6036, and a muscular skeletal system 6037. The skin system 6035 may depict the external surface of patients. The organ system 6036 may include various organ related systems, such as cardio, endocrine, neuro, or any other organ related system in a patient. The muscular skeletal system 6037 may include various aspects of the skeleton and muscles. A relatively generic image when zoomed in can show other detail images.

During operation, when a user wishes to save a blue print using the image mapping 502, the user may select an image from the image library using an image selection tab 6021 (details of tab not shown). Then the user is prompted with tab "Select Image systems/Symptoms" 6022 (details of tab not shown) to select the system, option set, and symptoms/choice list, as previously discussed. The user can select a specific image that in turn can represent a human body system such as Endocrine. This method can be used by a user to select any and all the symptoms of the human body system.

The user can also choose to select a small list of symptoms of the human body system instead of the full list. A "Select Systems/Symptoms tab 6023 may be selected by a user to show an interface where the user can select a marked image mapping 60215. Marked image mapping 60215 enables a user to select any part of an image for the purpose of associating a blue print with the marked portion of the image. Selection of a part or area of an image may be via a pointing device, such as a mouse, a touch screen, voice commands, text entry, or any other selection mechanism capable of conveying to the EMR system what part of the image has been selected. In one example, when a user selects a part of the image using the marked image mapping 60215, the user may be prompted with a list of symptoms for the selected part of the image so that the user can select the symptoms that apply to the blue print the user is saving to the selected part of the image.

A user has an option to choose any of the application users within the EMR system as an owner of the blue print using an owner selector 6027. In addition, a user can enter a name under which the blue print will be saved. The blue print name may be entered, for example, in a text box provided, and the user may perform a save function 6028, such as by clicking on a "save the blue print" button.

Figure 7:
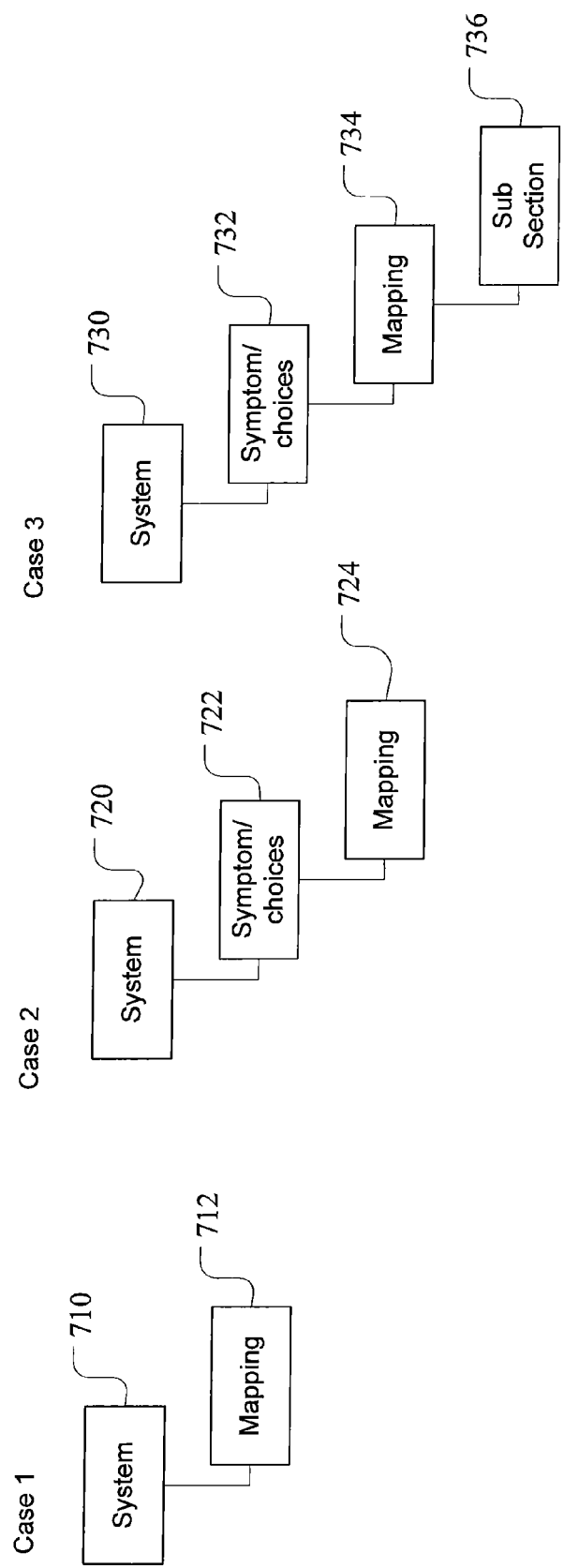
FIG. 7 is an example of hierarchal image mapping relationships within the electronic medical records system.

FIG. 7 is an example of the blue print image mapping hierarchy that makes the blue print engine flexible to associate an image area (can be a rectangle/polygon) to different levels of choice lists.

Case 1—On the image the user can associate a marking with a system 710, such as a human system at the system level. If the marking is associated with a system 710, all the option sets and choice lists/symptoms associated with the system may be inherited into to that marking 710. The blue print may also be mapped to at least one level of the hierarchical structure as previously discussed using the mapping 712 When the blue print is used by a user, such as a nurse/healthcare provider as part of an office visit, the user could add a choice with the option of "Save for future" (refer to FIG. 11) 1121. The new choice may be added to the option set and symptoms/choice list and will inherit the properties of this marking. Thus, the user does not need to explicitly mark the new choice to the image area again.

Case 2—On the image the user can associate a marking with a specific symptoms/choices list, 722 of a system 720, instead of the whole system as in Case 1. To associate at the symptoms/choice list level refer to FIG. 2 and FIG. 3. With this mapping 724 the marking is directly associated with the choice list/symptoms Case 3—As the same image can be used in different sections and sub sections of the application, restricting the image area association to a particular sub section allows reuse of the image. For example, the same heart image can show different choices when used in different sub sections of the "Subjective" section of the EMR system:

Subjective—section
CCHPI—(Chief Complaints & History of Present Illness) symptom choices like chest pain, shortness of breath, etc.—subsection
PMH—(Past medical history) disease choices like Heart failure, Atrial Fibrillation etc.—system
PSH—(Past surgical history) surgical choices like Open heart surgery, Angio plasty, etc.—system When a marking is associated with a section 736 and a sub-section 738, the image marking can be shown such that only that section 736 and sub section 738 are visible to the user with the association even when the association with the marking was made at the system 710, or the symptom/choices level 722, as previously discussed.

Figure 8:
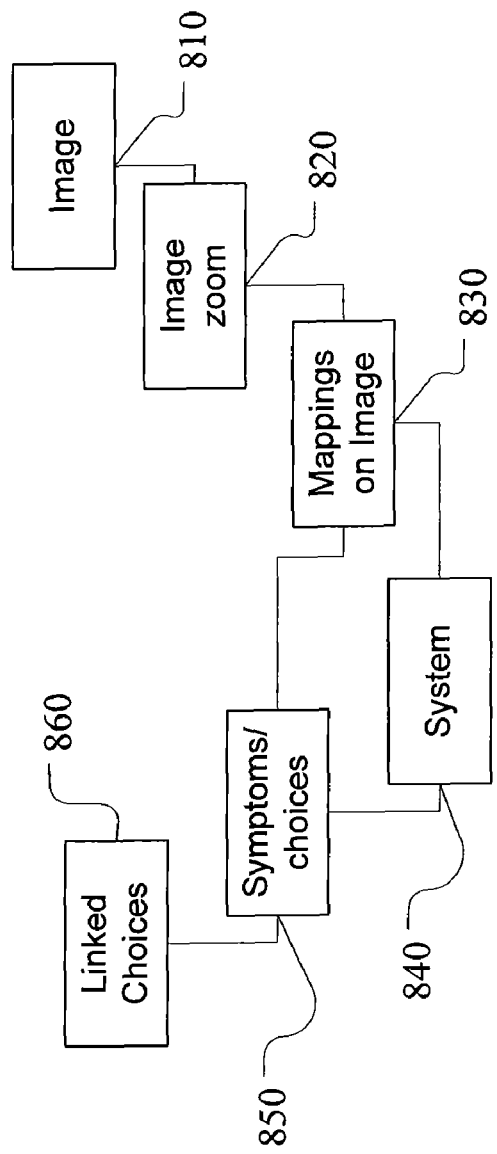
FIG. 8 is an example of a relationship between linked choices and image mapping within the electronic medical records system.

FIG. 8 describes an example relationship between the image marking and linked choices 860. This data relationship is used for the blue print launching from an image. Each marking on the image (image mapping) 830 may have an associated system 840, option set or symptom/choice set 850. A blue print 870 may be saved with a linked choice that is grouped with the system 840, option set and symptoms/choice list 850. Thus the choices 850 and the system 840 form a bridge between the blue print 870 and the image 810. The image has a property of orientation to describe the orientation from the user's point of view. For example consider an image showing the skin layer of a human, there could be five or more orientations—front, back, left, right, top. So we can rotate the image in 3D and have markings on the image that are specific to that view. For example, an image of a human eye may be included in a front view of the skin layer of the human image, the spine may be included in the back view, and skin will be included in both the front and back view of skin layer of the human image. Each mapping can have their own list of symptom choices (rash, swelling, redness, itching eyes) or Systems (Dermatology, Ophthalmology etc.) associated. Based on the choice selected by the user, the corresponding blue print will be launched.

Figure 9:
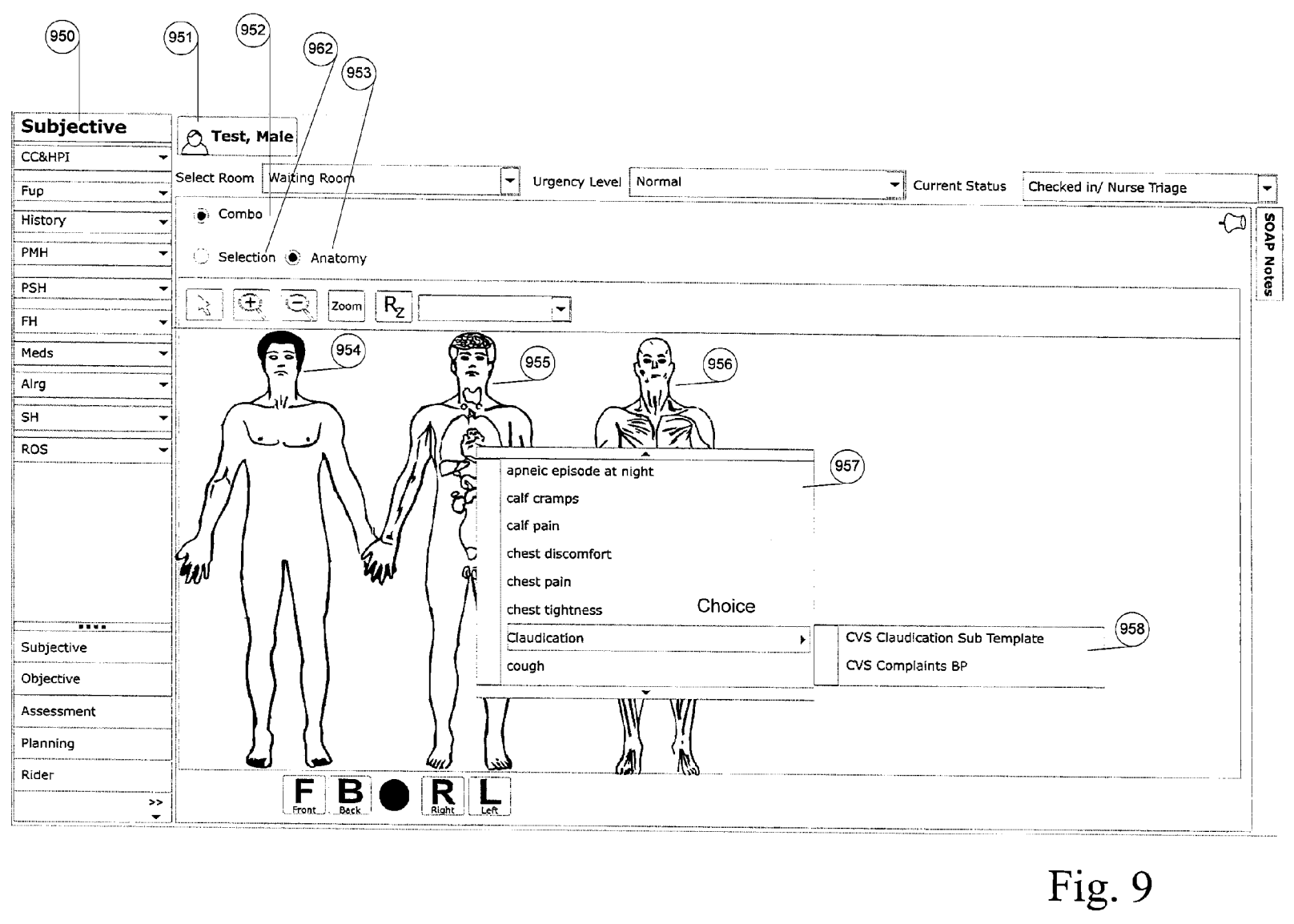

FIG. 9 depicts an example graphical user interface for launching a blue print from the sections and sub sections by an end user. In other examples, other forms of user interface and or graphical displays may be used to provide similar functionality. To give brief details on sections, sub sections and images, a section is made up of subsections, as previously discussed. Each marking on an image may be associated with the sections and/or sub sections, which was described with reference to FIG. 7.

When a user (Nurse/Provider) selects a patient for whom the visit note is to be made or updated, the screen as depicted in FIG. 9 may be shown on the display device. This screen may be referred to as nursing triage. The section under which the visit note is categorized is identified as a subjective section with a section identifier 950. A sub section selector area 960 may also be included in the display. The subjective section may include associated sub section selectors in the sub section selector area 960. The sub section selectors may be selected by a user in order to select one or more subsections. In the example of FIG. 9 the sections includes associated subsections like a CCHPI selector 960 for selecting the CCHPI subsection as well as others that are associated with the subjective section within the EMR system.

In FIG. 9, the sub sections may be loaded and displayed on a left side menu of the user interface for selection by a user. A default anatomical human image configured for and associated with the subsection may be loaded in an image section 952. The default anatomical human image may be configured by the user of the EMR system for each of the sub sections. For example, if the provider is a Family practitioner then a combo anatomical human image (combination of all body systems) may be associated with the CCHPI subsection and shown as depicted in FIG. 9. In another example, if the provider is a cardiologist then an anatomical human image of a heart may be associated with the CCHPI subsection and shown in the image section 952.

Depending on the patient gender (male/female) as determined from patient records stored in the EMR system, the image is rendered from the anatomical human image library. Every anatomical human image stored in the EMR system may be categorized with respect to human anatomy, in the example image depicted in FIG. 9, three different anatomy categories are combined in to one single anatomical human image: a Skin system image 954, an Organ view image 955 containing Cardio system, Endocrine system, Neuro system and the like, and a Muscular Skeletal system image 956. In other examples, one or more images representative of any human anatomical image may be displayed.

As described in FIG. 8, each image has user selectable orientations (front, back, left, right), as previously discussed. Areas of the image may be marked and linked to specific human anatomy system, e.g. the heart area may be linked to cardio vascular system. Each human anatomy system may have linked choices for the user to select that would launch the corresponding blue print. A view slider (not shown) may enable a user to rotate the human anatomical image in three dimensional (3D) space. In addition, a cross section slider (not shown) may be selected by a user to slide between the human anatomical images, or layers, for example from the skin system image 954 to the muscular skeletal system image 956 to the Organ view image 955.

In FIG. 9, the selected patient may be shown as patient identifier tab 951 that incudes patient identifying information, such as a patient picture thumb nail, patient name (patient last name, patient first name), or any other patient specific information. To launch a blue print the user may select a launching mechanism form the user interface. In FIG. 9, the user has an option to use either a selection launcher 962, or an anatomy launcher 954.

When the selection launcher 962 is selected by a user, a selection view controller stored in the memory is executed by the EMR system. The selection view controller is configured to access the data structure library and the blue print library and generate a selection screen for a particular patient on a display of the EMR system. The selection screen may include an evaluation type indication, a human body system indication, a chief complaint indication and a medical condition associated with the chief complaint indication, as previously described. The medical condition may be included in a predetermined list of medical conditions and may be associated with a blue print containing patient specific data. The selection view controller may perform the functionality of the EMR system herein described.

When the anatomy launcher 954 is selected, an anatomy view controller stored in memory and executable with the EMR system. The anatomy view controller may generate anatomical images and perform the functionality herein described. A user may use anatomical human images generated with the anatomy view controller to launch a desired blue print for a particular patient. In one example, a user may hover a pointing device, such as a mouse over any one of the markings or predefined areas into which a human anatomical image is divided. In response, the anatomy view controller may, retrieve an option set 329 containing a choice list 330 of control variables, as previously discussed with reference to FIG. 3. The option set may be a linked set of control variables that shows the symptoms or medical conditions to the user in a choice list 957. In FIG. 9, all the marking names (body sites) may also be shown in a drop down list 959 for quick navigation to the marking or body sites. Thus, for example, a user may either select heart or lungs from the marking over the depiction of the heart and lungs in the organ view image 955, or may select heart or lungs from the drop down list 959. In other examples, any other mechanism or format may be used to perform selection of a blue print from a human anatomical image or from a list.

For each symptoms/choice list 957, all the blue prints saved in association with the selected control variable are aggregated in a blue print list 958. A user may then select a desired one of the blue prints from the blue print list 958 to launch the selected blue print. Every choice list 957 may include an association with at least one blue print, therefore linking the associated blue print with a respective marking on the human anatomical image. Multiple blue prints can be associated with a single symptom, medical condition or control variable. If there is only one blue print for a particular symptom, when the symptom is selected, such as by clicking the symptom, the associated blue print is launched. If, for example, there is more than one blue print associated with a control variable, the user may be prompted with the blue print list 958 to choose one of the blue prints, as illustrated in FIG. 9. A user can choose a relevant blue print from the blue print list 958 in order to launch the blue print, and fill the blue print with patient specific content.

A blue print can be launched using the selection view illustrated in FIG. 15. Using selection view, a user can find the symptom to launch the blueprint to collect the information from the patient regarding their symptoms and problems. Predefined sets can have multiple option sets included in an option set list 1501, each option set in the option set list 1501 can have multiple symptoms displayed in a symptom list 1502 upon selection of the respective option set. For example, in FIG. 15, the option set "Chief Complaints—CVS (CVS)" is selected from the option set list 1501, and the corresponding symptoms are displayed in the symptom list 1502. Many blueprints 1503 can be associated with a symptom in the symptom list 1502. A user can select different symptoms from the symptoms list 1502 to launch different blueprints during a patient visit.

Each blueprint is user dependent, so different users can use the same blueprint on the patient visit notes. As illustrated in FIG. 15, option sets are shown to a user in the symptoms list 1501. On selecting one of the option sets, the EMR system shows multiple associated symptoms in the symptoms list 1502. On selecting a symptom from the symptom list 1502, the blue print list 1503 is shown to the user. On selecting a blue print from the blue print list 1503 the blue print is launched. In one example, the user can only see the list of blue prints that he/she has permission to. The blue print permissions are set during the blue print saving process as previously discussed with reference to FIG. 5.

Figure 10:
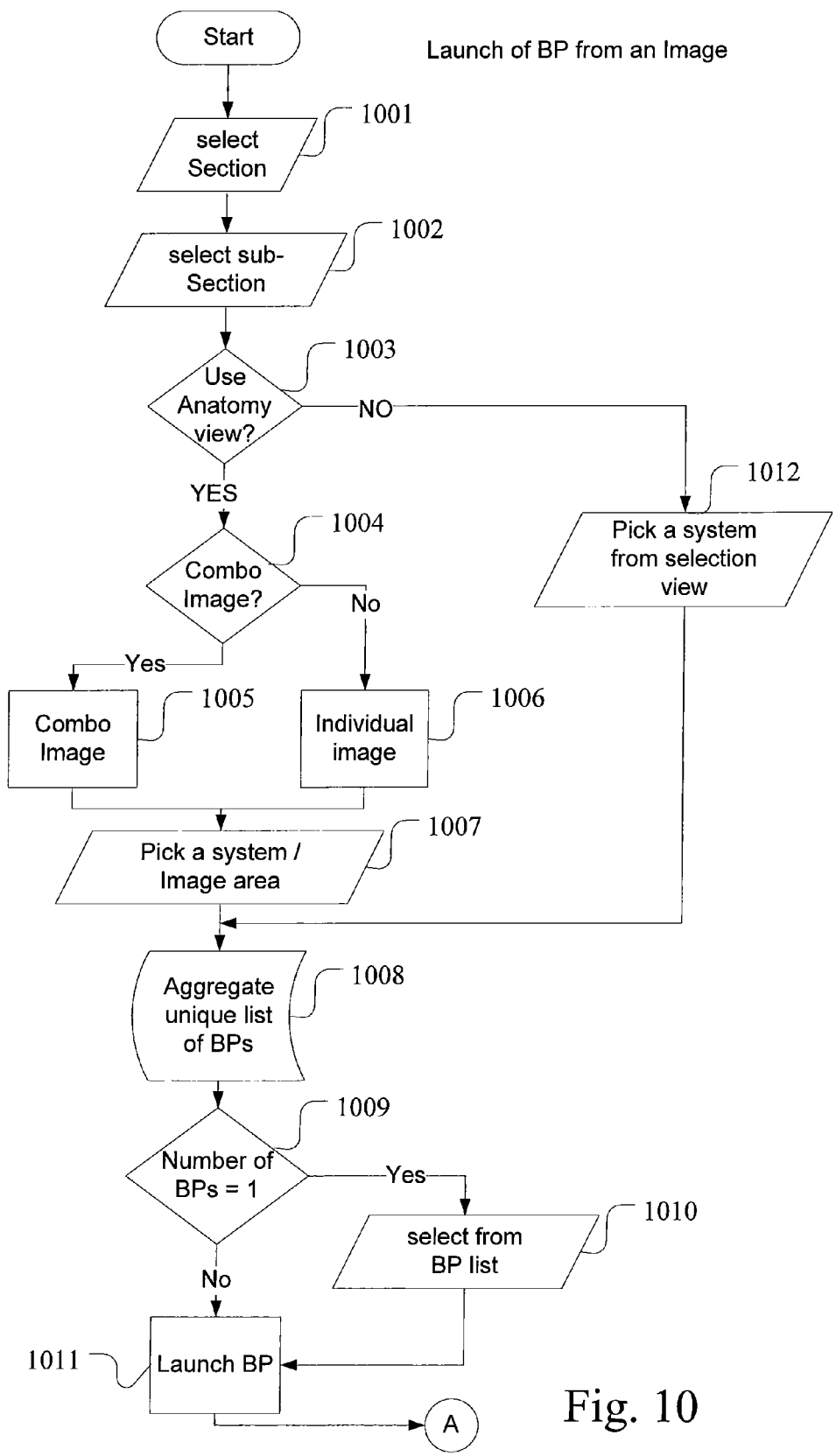
FIG. 10 is an example operational flow diagram describing a flow of events to launch a blue print using a human anatomical image.

FIG. 10 is an example operational flow diagram describing a flow of events that take place to launch the blue print using a human anatomical image with reference to FIGS. 1-9. At block 1001, a user may select the section 410, 440, 480. The selected section may be indicated in the section identifier 950. Each section 410, 440, 480 is grouped or associated with one or more sub sections 420, 450, 482. All the sub sections 420, 450, 482 can be shown to a user in the sub section selector area 960. At block 1002, a user may select one of the sub sections from the sub section selector area 960. The processor of the EMR system may launch the images associated with the selected sub section. At block 1003, the EMR system may give the user an option to use either a selection view or a human anatomical image anatomy (image view). For example, the user may select either the selection launcher 962, or the anatomy launcher 953 from the user interface of FIG. 9.

If the user selects the Anatomy view, at block 1004, the processor of the EMR system may retrieve and display an image selection list. The image selection list may show an entire anatomy category of available images to the user based on the selected sub-section. In this example, the user may select from either individual anatomical human images or a combo anatomical human image, as previously discussed. If the user selects any one of individual anatomical human images, such as in the categories of skin, skeleton, muscle, at block 1006 the selected individual anatomical human image is displayed to the user. If, on the other hand, the user selects the combo anatomical human image, at block 1005, the combo anatomical human image is displayed to the user. Whichever of the individual anatomical human images, or the combo anatomical human images are selected, each of the images depict marked areas on the respective image that are representative of the existing of patient specific data in the form of a blue print. At block 1007, the user may select a sub section or image area from the marked areas of the displayed image.

If at block 1003, the user chose the selection launcher 962 instead of the anatomy launcher 953, at block 1012 the user may chose a system 430, 460, 484 from a selection view containing a listing of systems 430, 460, 484 available in the EMR system that are associated with the selected section 410, 440, 480 and sub section 420, 450, 482. As previously discussed, upon selection of a system 430, 460, 484 either based on a mark on a human anatomical image, or based on selection of a system 430, 460, 484 from a selection list, the EMR system may display an option set 470, 486 for the selected system 430, 460, 484. At block 1008, a plurality of control variables associated or linked with the respective systems 430, 460, 484 by the option set 470, 486 may be aggregated into a choice list 957 to represent a unique list of blue prints (BPs) for that choice from the selection view or image location in the image view. At block 1009, it is determined if a symptom, or control variable, or medical condition has more than one blue print associated or linked. If more than one blue print is linked, at block 1010, the EMR system retrieves and displays a blue print list for the user to choose from at block 1010. After the user selects one of the linked blue prints, or if the number of linked blue prints is only one, then the blue print is retrieved and launched based on user selection at block 1011.

Figure 11:
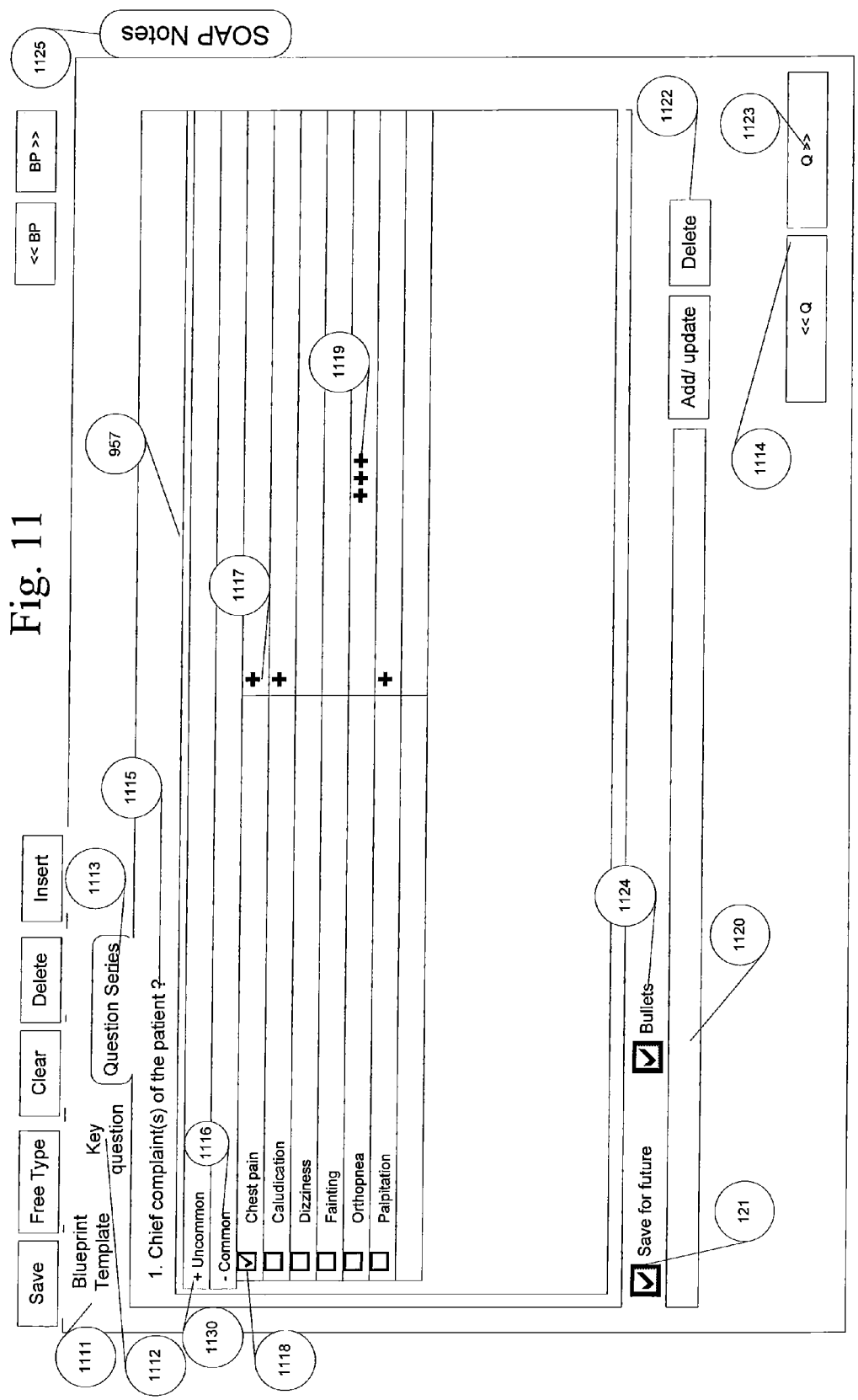
FIG. 11 is an example graphical user interface for using a launched blue print to organically grow choice data.

FIG. 11 is an example graphical user interface for end user usage of a launched blue print and organic growth of choice data. Once a blue print is launched, the blue print may be presented to the user in any of a number of different data perspectives for population/configuration of patient specific data in order to create and/or revise a visit note. As discussed later with reference to FIG. 14, in one example, the different data perspectives may include a blue print template perspective, a key question perspective and a question series perspective. Selection of different data perspectives by a user may be accomplished using different selectors. In FIG. 11, the example selectors include a template blue print selector 1111, a key question selector 1112 and a question series selector 1113 in the form of a series of tabs. In other examples, any other form of selectors may be employed. A user may have an option within that user's profile to set any of the data perspectives as default view for each section and sub section, so that that data perspective will be used the next time the user visits a particular section or subsection.

Selection of the different data perspectives provides the user with one of a plurality of corresponding views. A template blue print view resulting from selection of the template blue print selector 1111 may present one or more paragraphs and one or more corresponding sentences included in the selected blue print with the replaceable fields as blanks. All the control variables available to populate the replaceable fields may also be available to the user, such as in the form of a list or pop-up window. In addition, manual entry of unlinked control parameters by the user, such as by typing or selection of keywords from a list, may also be enabled. As previously discussed, population of the replaceable fields showed to user allow the user to complete the sentences by filling in the blanks to create a visit note. A user may select a replaceable field, such as by clicking on the field, and may fill in the blanks by selection of a control variable or input of a control variable value. Population of the replaceable fields results in completion of the sentences within the blue print such that a patient specific visit note is created.

A key question view resulting from selection of the key question selector 1112 may present all the linked control variables content of the blue print in a question and answer format. As discussed with regard to FIG. 2, each of the sentences in the blue print may be associated with one or more control sets and one or more key questions. The key questions can be displayed to a user one at a time. Alternatively, groups of questions may be displayed together. A user may select a question that they wish to answer, such as by clicking on a fill in the blank(s) to input/key in a control variable value from the control set. The control variable value may be selected, or manually input as previously discussed. Once the user has selected values from the control set, the selected values may populate the fillable fields as answers to the key questions. In addition, the selected control variables may populate the fillable fields in the sentences of the blue print to create a patient specific visit note.

A question series view resulting from selection of the question series selector 1113 may present one or more key questions at a time with the control variables of the control set available as selections to provide an answer to the key questions. In one example, one question at a time with key question and control set for selection may be displayed to a user. The user may move between the questions based on user commands. In one example, movement between questions, such as moving to a next question and back to a previous question may be performed at any point of time with a back selection (<<Q) 1114, and a forward button (Q>>) 1123.

As previously discussed, the control set may be associated with one or more key questions 1115 and a choice list 957 of symptoms, medical conditions or control variables. The choice list 957 may include presentation of a common list 1116 of control variables, and an uncommon list of control variables 1130. One or more Sub blue prints may also be associated with any one or more of the control variables included in the choice list 957. In one example, representation of the existence of a sub blue print may be shown with a "+" symbol 1117 from which the sub blue print may be launched. In other examples, any other indicator or mechanism capable of alerting a user to the existence and providing the capability to launch the sub blue print may be implemented.

A user can select multiple choice list values (control variables), or a single choice list value (control variable). The control set may allow the user to select the single value or multiple values using a value selector indication 1118. If a user selects a sub blue print, populates the fillable fields of the sub blue print with values and closes the sub blue print, the EMR system may indicate that the sub blue print has been completed with a completed indication 1119. For example, in FIG. 11, the completed indication 1119 may be in the form of "+++" to indicate to the end user that the sub blue print has been updated with patient specific information as part of a visit note. The filled sub blue print content may be associated with the choice list 1119 via a corresponding control variable.

If the user did not find the selecting symptom (control variable) or choice list in the control set, the user can add the symptom/choice list to the control set using a manual data entry point 1120, such as a text box. In other examples, a pick list, a database selector, or any other mechanism may be used to add a choice list and/or control parameter to the control set. A user may also have an option to save a newly added choice list/symptom to the control set definition by a save selection 1121. In FIG. 11, the save selection option 1121 is indicated as a "Save for future" check box. A newly added choice list or control variable that is saved using the save selection option 1121 is saved within a control set against the current patient and visit context as part of a visit note. If the user does not want to save a newly added choice list or control variable, the user can de-select the save selection 1121. Using the save selection option 1121, a user may add new choice lists and/or new control variables to a blue print in an organic fashion during operation of the EMR system. In addition, a user can delete an added symptom, medical condition, or choice list from a control set using a delete function 1122, such as by selecting the data to be deleted and clicking on a "Delete" button depicted in FIG. 11. The user may also format newly added data using format controls 1124. In the example of FIG. 11, the user has an option to present the data in bulleted format, which will show newly added control variables one after one as a separate line or as a new sentence in the respective blue print.

The control set selection may be substantially similar either from the key questions view or the blue print template view since these two views may have similar data perspectives of the same underlying question/answer structure.

Figure 12:
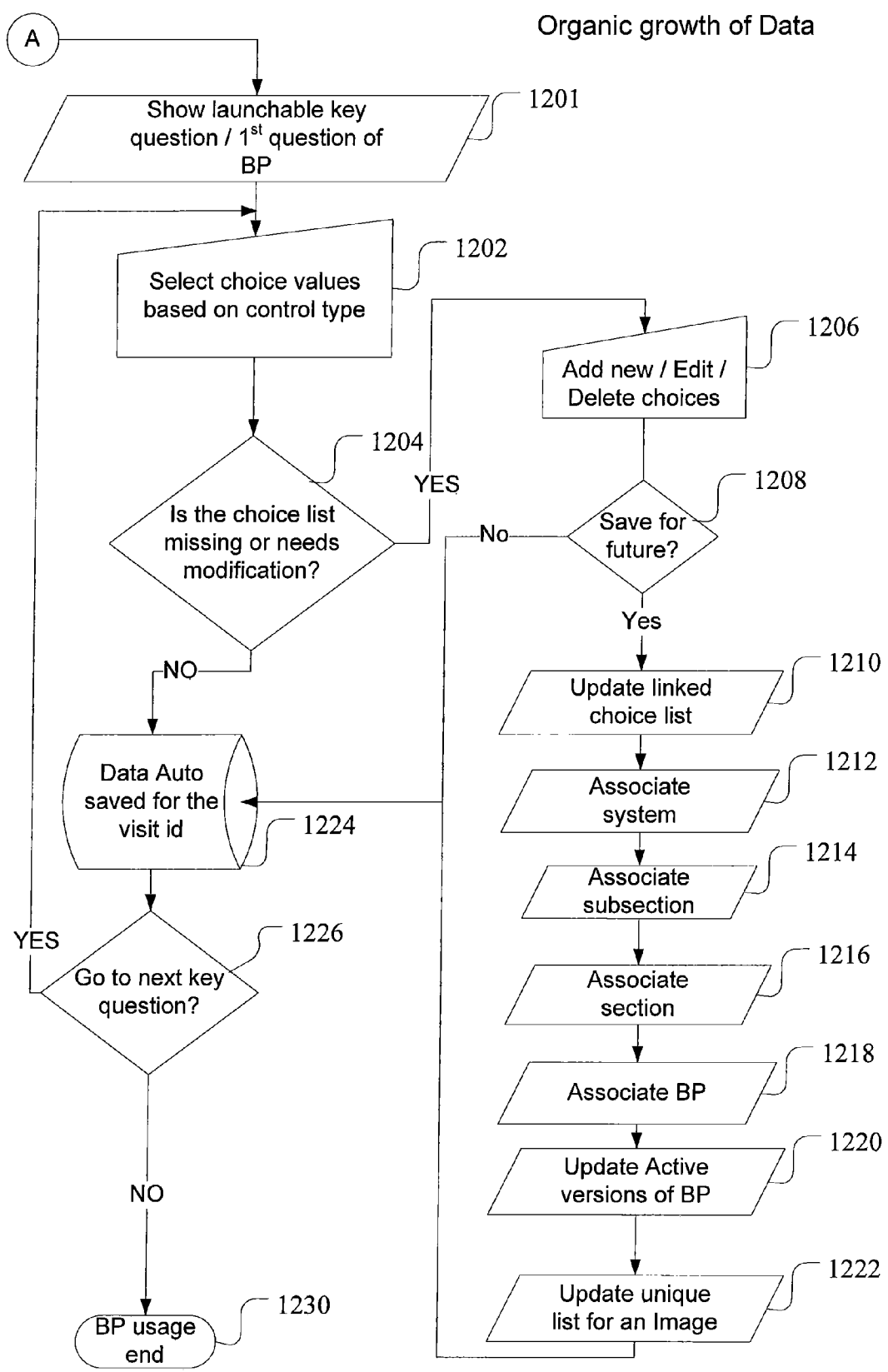
FIG. 12 is an example operational flow diagram of blue print usage.

FIG. 12 is an example operational flow diagram depicting a workflow of blue print usage. FIG. 12 may be considered as a continuation of the work flow depicted in FIG. 10 since blue print usage may follow blue print launch. In other examples, other operational flows to launch a blue print may be utilized in conjunction with the example operational flow depicted in FIG. 12.

Once a blue print is launched, at block 1201 the EMR system may generate a launchable key question or a first question of a blue print template to update or generate a visit note for a particular patient. In addition, the EMR system may show a default view of a corresponding sub section with one or more first question control set values or control variables. As previously discussed, the system defined control variables are linked, or associated with the fillable fields in the sentences of the blue print when the blue print is created or modified. Based on the different control types selected for each of the control variables, at block 1202, a choice list of symptoms representing the control variables may be presented to the user for selection.

At block 1204, it is determined if a choice list and/or one or more control variables is missing from a control set, or needs modification in order to correctly answer a question in the blue print or a key question launched for a particular patient. If the user cannot find the desired choice of a control variable in the choice list of the control set, the choice list is absent from the control set, or the choice list or control variables needs to be modified at block 1204, the user has an option to add the missing control variable(s) or choice list to the control set, edit an existing choice list, or delete control variables from the choice list at block 1206. At block 1208, it is determined if the user wants to save the control set for the entire system (save for future) or just for the particular patient after completion of adding new, editing, or deleting control variables or choice lists. If the user does not want to save the changes to the control set definition for the entire EMR system, the user may unselect the "save for future" checkbox 1121. If the user unselects the "save for future" check box at block 1208, at block 1224 the new choice list may only be updated with the revised data for this blue print template and the data will be saved to only that visit note for that particular patient. Accordingly, the changes are not provided as an update to organically grow the EMR system, and are instead used only for the particular control set in the context of a visit note for a particular patient.

If, on the other hand, when the user selects "save for future" check at block 1208, the EMR system may update the control set definition to update the associations. Specifically, at block 1210 the EMR system may update the linked choice list. At block 1212, the EMR system may associate the revised control set, namely the revised choice list included in the option set 470, 486, with any of the systems 430, 460, 484 present in the EMR system. The EMR system may also associate the revised control set with the subsections 420, 450, 482 present in the EMR system at block 1214. At block 1216, the revised control set may be associated with the sections 410, 440, 480 of the EMR system, by updating the sections 410, 440, 480.

The system may then update the blue print definition stored in memory at block 1218, and update the active versions of the blue print at block 1220. The EMR system may then update a unique list used for image marking of the human anatomical images stored in the image library at block 1222 such that the system, option set, and symptom or choice list associated with each of the markings on each of the human anatomical images stored in the system are updated.

If, on the other hand, the user finds the desired choice to complete the launched key question or blue print fillable field in the choice list at block 1204, then the choice list needs no modification and the system saves the selected values at block 1224 in association with the fillable field as part of a sentence in a visit note for a particular patient. At block 1226 it is determined if the user wants to navigate to the next key question or the next question in the blue print template. If yes, then the system will loop back to block 1202 and repeat the operation. If, however, the user does not want to proceed to the next question then the blue print usage ends at block 1230.

Figure 13:
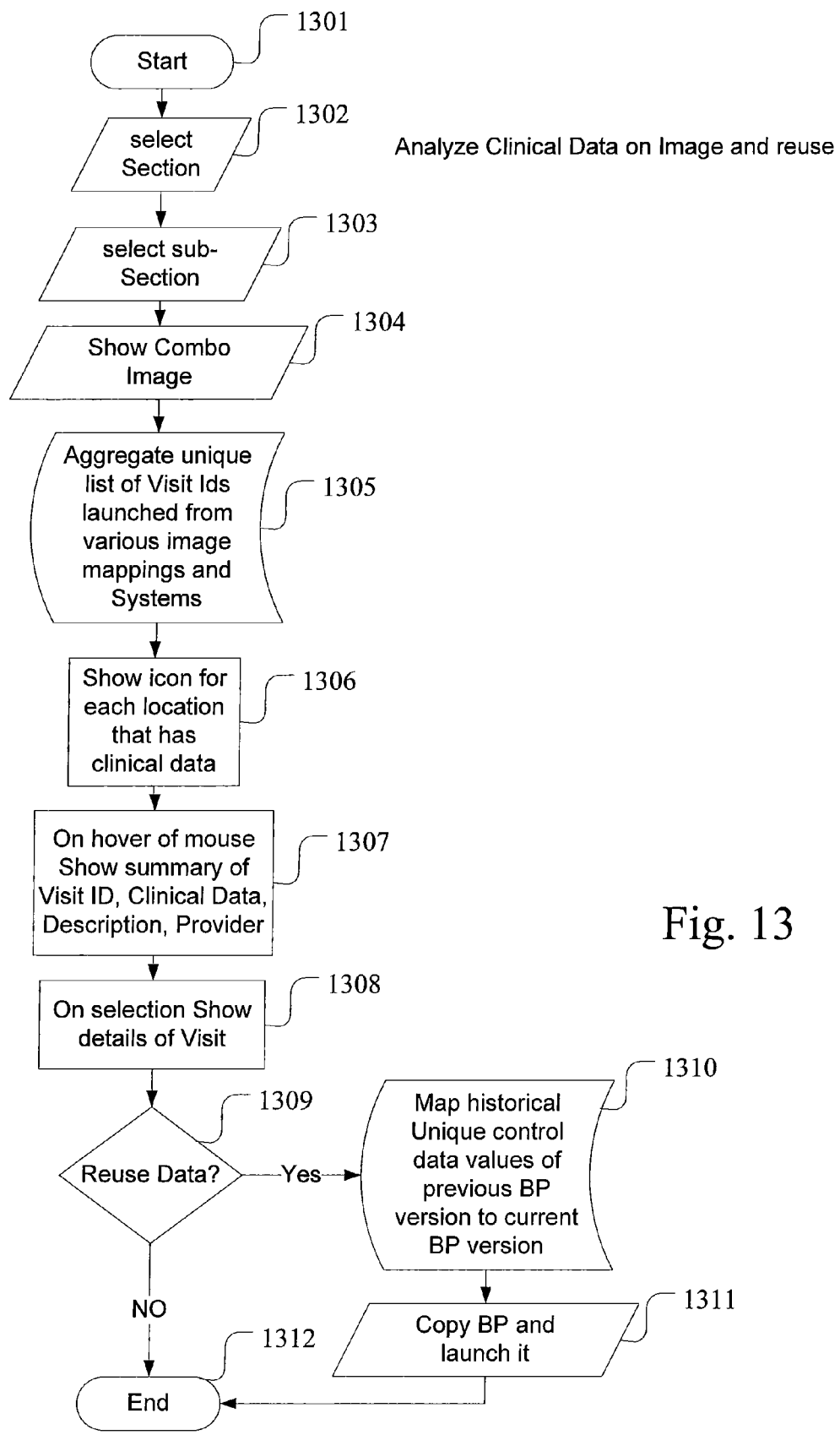
FIG. 13 is an example operational flow diagram for associating reusable visit data with markings on a human anatomical image.

FIG. 13 is an example operational flow diagram that represents the work flow of associating reusable visit data with markings on the human anatomical images for a particular patient. As previously discussed, the data collected from various blue prints for a particular patient may be aggregated or otherwise organized by being brought back onto one or more human anatomical images for easy comprehension and review by the provider/nurse.

For example, assume that a patient visits a nurse or other healthcare provider for a follow up visit due to preexisting knee pain. To understand the history of the patient, the provider should read and understand all the previous visit notes for this patient, including, for example, visit data for fever, chest pain, a hip replacement and knee pain. These visit notes may span multiple visits over an extended period, such as one year or longer. It is otherwise cumbersome for the provider to extract visit related data for any part of the patient's skeletal system from among the other different documented medical issues of the patient. In this example, to maximize efficiency of the user, quick and efficient retrieval and review of any hip replacement and knee pain complaints from previous visit notes for this particular patient would be of great benefit to the healthcare provider and the patient.

With the EMR system the patient specific data of the previous visit notes may be brought back to the user on a human anatomical image. The locations within the human anatomical image that have data behind them may be marked with an identifier, such as red icon to indicate there is patient specific data available for that area of the human anatomical image. As such, the user/healthcare provider can select the marked identifier, such as by hovering a mouse over any red icon in order to get the visit data specific to that anatomy location. Using the human anatomical image the efficient of the user may be increased substantially since the user need not go through the fever and chest pain visit notes that are not related to the reasons for the patient's current visit. This data aggregation is made possible by the blue print engine operating within the EMR system structure. The provider can actually decide to reuse the data from a previous visit by this patient in the current visit with a single click.

In FIG. 13, upon a patient arriving for an office visit, a user, such as a nurse or other healthcare provider may begin the workflow operation at block 1301. At block 1302, the user may select a section appropriate to the purpose of the patient's visit, such as "Subjective." Each section is grouped with a set of sub sections, as previously discussed, and all the sub sections associated with the selected section may be shown to user.

At block 1303, the user may select one or more of the subsections. The EMR system may launch the human anatomical images associated with the sub section, and give the user an option to use anatomy (image) view. For example, at block 1304 the EMR system may display the combo human anatomical image previously discussed with reference to FIGS. 6 and 9. If the patient has past visit data, the EMR system may pull all the previous visit data using a list of unique visit identifiers for the particular patient at block 1305. At block 1306, the image may be populated with the previous visit data in the form of identifiers, such as icons, positioned on the image in the vicinity of each location for which clinical data is available.

A user may select information related to a particular medical condition of a patient, such as by hovering with a mouse over those identifiers on the human anatomical image at block 1307. Information provided to the user from the EMR system in response to user selection of information may include, for example, a summary of an office visit that includes a Visit ID, Clinical Data, a Description of the problem, and an identification of the Provider. The information may be presented to the user via a graphical user interface or any other display based mechanism. At block 1308, based on user selection, the details of a previous visit may be displayed by the EMR system.

The user may be prompted if they want to reuse the data from an existing visit note at block 1309. If the user chooses yes then the EMR system may map historical unique control variable data values of a previous blue print version to a current blue print version at block 1310. As previously discussed, the existence of an older version of a blue print and a newer version of a blue print may be due to organic growth in the EMR system since the previous blue print was created for the particular patient. The versioning of the blue prints may be leveraged in the EMR system since some questions in the previous version of a blue print may have been deleted or modified in newer versions of the blue print. In one example, only the answers for the questions that match the previous visit blue print may be copied to a current version of the blue print that is now available. This can maintain data integrity in the system. Alternatively, in addition to copying the answers to the common questions to the new blue print, the system may also important the entire sentences and answers that were omitted from the newer version of the blue print. In still other examples, any other mechanism or routine may be used to reconcile differences between versions of the same blue print.

After the current version is reconciled with the previous version of the blue print, the newest version of the blue print may be populated with the patient specific data and may be copied and launched for the current visit at block 1311. The user can then modify the answers in the launched blue print as desired based on the office visit. If the user answers no for reuse of a blue print from an existing office visit of the specific patient, then a blue print history screen may be closed. This ends the work flow for retrieving the data on an image and reusing it as required.

Figure 14:
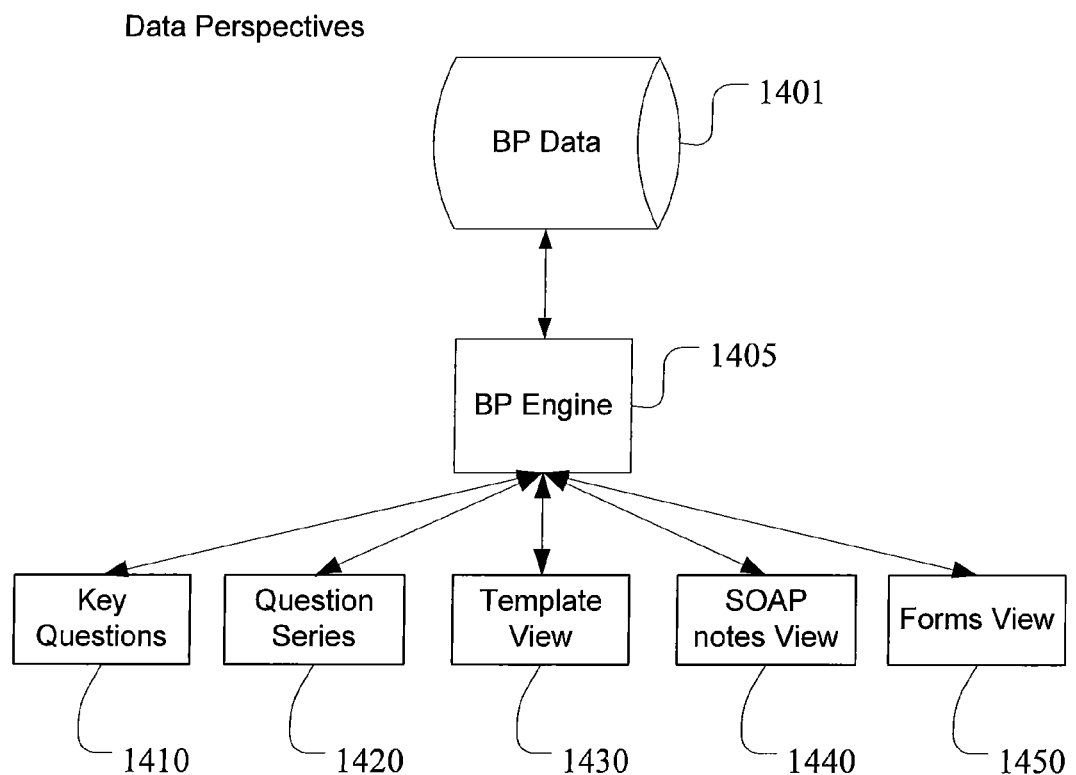
FIG. 14 is an example block diagram representing the functionality of blue print engine within the electronic medical records system.

To make the data entry easy for the user the EMR system includes a number of different data perspectives. FIG. 14 is an example block diagram representing the blue print engine content rendering in different formats for the user. In one example, the data modified in any of these data perspectives may similar change the common blue print content. Accordingly, the user can switch between these perspectives at any point yet see the data (answers for the questions) remain are all in sync.

In FIG. 14, a blue print data storage 1401 may cooperatively operate with a blue print engine 1405 to store and retrieve saved data. The data retrieved from the blue print data storage 1401 may be presented to the user using the blue print engine frame work, as previously discussed. Specifically, blue print content when launched can be presented in any of the following formats:

Key questions 1410—A list of questions—when the user clicks the question a form with answers will pop up. Once they user fills the answer the user is brought back to the main screen with a list of questions.

Question series 1420—A list of questions presented in a sequence where the user can answer and hit next to save the current answer and go to the next question in sequence.

Template view 1430—In this perspective the sentences of the blue print is presented as a paragraph with dashes where the answers need to be filled. When the user clicks the dash a form pops up with the answer controls.

SOAP notes view 1440—This perspective is similar to template view but it has content formatting—color, indent, font etc. The user can also jump to a particular BP using a quick access list of BP's loaded.

Forms View 1450—This perspective combines the questions and answer controls in one form. For e.g. each question will have the answer choices expanded so the user can directly answer without opening a new window.

During operation, the blue print engine 1405 may synchronize the data between different perspectives when the user is switching between them. Since each question in the EMR system has an ID that is unique to that blue print, when the perspective is switched the blue print engine 1405 may map the answers based on the unique id and renders it.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. An electronic medical records system, comprising:
   a processor;
   a computer readable storage media that comprises instructions stored in the computer readable storage media that are executable with the processor, the instructions comprising:
   instructions to prompt a user to select one of a selection view and an anatomical view;
   instructions to display a first list of pre-defined medical conditions in response to receipt of a view selection command indicative of a user selection of the selection view;
   instructions to retrieve and display an anatomical human image in response to the view selection command being indicative of selection of the anatomical view;
   instructions to display a second list of pre-defined medical conditions for an area of the anatomical human image in response to an area command indicative of selection by the user of the area of the anatomical human image;
   instructions to display a list of blue prints that are associated with a selected one of the pre-defined medical conditions, each of the listed blue prints including control variables, at least some of which appear in multiple of the listed blue prints;
   instructions to launch a blue print in response to receipt of a signal indicative of a selection of the blue print from the list of blue prints;
   instructions to retrieve and display any one of a blue print template, a key questions list, or an interactive question series that correspond to the launched blue print associated with the one of the pre-defined medical conditions associated with either the selection view or the anatomical human image;
   instructions to receive user entry of patient specific data into a selected one of the blue print template, the key questions list, or the interactive question series for a particular patient to populate the launched blue print; and
   instructions responsive to user entry of the patient specific data to generate a predetermined sentence structure having one or more fillable data locations mapped to receive respective control variables, the one or more fillable data locations positioned within predetermined sentences forming a paragraph that is stored in connection with the launched blue print, at least some of the one or more respective control variables also mapped to fillable data locations included in other blueprints associated with the one of the pre-defined medical conditions and used to generate the predetermined sentence structure in connection with the other blueprints.

2. The electronic medical records system of claim 1, wherein the computer readable media further comprises instructions to prompt the user to select one of the blue print template, the key questions list, or the interactive question series as a vehicle to receive and store the patient specific data.

3. The electronic medical records system of claim 1, wherein instructions to retrieve and display an anatomical human image further comprise instructions to display a first anatomical image representative of an external body surface view, a second anatomical image representative of an organ view, and a third anatomical image representative of a muscular skeletal view.

4. The electronic medical records system of claim 1, wherein the control variables comprise an automatic control variable populated by the system with pre-existing patient specific data, a manual control variable populated with the user entry of the patient specific data in response to a user selection of the patient specific data from a predetermined choice list of variables, and a semi-automatic control variable automatically populated by the system with additional patient specific data in response to receipt by the system of the user entry of the patient specific data.

5. The electronic medical records system of claim 1, wherein instructions to receive user entry of patient specific data further comprises instructions to modify the blue print to add additional predetermined sentences having fillable data locations populated with the patient specific data using control variables, the patient specific date received via one of the blue print template, the key questions list, or the interactive question series.

6. The electronic medical records system claim 5, wherein the instructions further comprise instructions to display a key question and a choice list comprising a plurality of user selectable predetermined patient specific conditions that are control variable choices, each of the control variable choices are a possible answer to the key question.

7. The electronic medical records system of claim 6, wherein the plurality of user selectable predetermined patient specific conditions are a first plurality of user selectable predetermined patient specific conditions, and the instructions further comprise instructions to display an option list comprising a second plurality of user selectable predetermined patient specific conditions that are also control variable choices for possible answers to the key question, and instruction to receive a linking command indicative of a linking request received from the user to link the choice list and the option list within the blue print.

8. The electronic medical records system of claim 7, further comprising instructions to add one of the second plurality of user selectable predetermined patient specific conditions to the choice list as a control variable choice in response to receipt of an add command indicative of an add request received from the user.

9. The electronic medical records system of claim 1, wherein the instructions to retrieve and display an anatomical human image in response to the view selection command being indicative of selection of the anatomical view further comprise instructions to display a patient gender in the anatomical human image based on the patient gender being indicated by one of the control variables.

10. The electronic medical records system of claim 1, further comprising instructions to dynamically modify control variables in a plurality of the blue prints, in response to a user entry into one of the blue print template, the key questions list, or the interactive question series.

11. The electronic medical records system of claim 1, further comprising instructions to dynamically modify at least one of pre-defined medical conditions and image mappings based on modification to one of the blue prints.

12. The electronic medical records system of claim 1, further comprising instructions to dynamically associate a control variable with launch of the blueprint in response to receipt of an indication of a user input of a use for launch selection being associated with the control variable.

13. A method of creating electronic medical records comprising:
   displaying with a display device a first prompt to a user to select one of a selection view or an anatomical view of a human body;
   in response to receipt from a selection device of a view selection command representative of selection by the user of the selection view:
      retrieving from a database and displaying a list of pre-determined medical conditions;
      displaying with the display device a second prompt to the user to select one of the conditions from the list of pre-determined medical conditions; and
      in response to receipt from the selection device of a signal representative of selection by the user of a condition from the list of pre-determined medical conditions, retrieving a list of blue prints that correspond to the condition selected;
   in response to receipt from the selection device of an anatomical view command representative of a user selection of the anatomical view:
      retrieving from the database and displaying an anatomical human image that includes selectable areas associated with a respective conditions list specific to a respective one of the selectable areas; and
      in response to receipt from the selection device of an area command representative of a user selection of one of the selectable areas from the anatomical image and the condition from the respective condition list, retrieving the list of blue prints that correspond to the condition selected;
   launching a blue print from the list of blue prints;
   displaying with the display device a third prompt to the user to select one of a dynamic question series format, a key question format, or a blue print template entry format configured for entry of patient specific data into the launched blue print;
   receiving the patient specific data as user entered data into a selected one of the dynamic question series format, the key question format, or the blue print template entry format;
   modifying the launched blue print using the user entered data to select a control variable, the launched blue print comprising a plurality of predetermined sentences formed into paragraphs, the predetermined sentences comprising a plurality of fillable data locations mapped to different control variables, the control variables used to complete the predetermined sentences in response to selection based on the user entered data; and
   completing predetermined sentences included in a sentence structure of other blue prints that have fillable data locations mapped to the control variables populated with the patient specific data.

14. The method of claim 13, further comprising displaying a predetermined question to the user, receiving a user selection of an answer to the question that is the patient specific data, and populating the launched blue print with a new predetermined sentence associated with the predetermined question that includes a control variable selected based on the corresponding answer.

15. The method of claim 13, further comprising a user initiating saving of the blue print from one of the selection view and the anatomical view, wherein saving the blue print with the selection view comprises associating the blue print with at least one level of a hierarchical structure comprising an evaluation type, a human body system, a chief complaint and the list of pre-determined medical conditions, and saving the blue print with the anatomical view comprises associating the blue print with one of a plurality of predefined areas of the anatomical human image by selection of the one of the predefined areas, and further associating the blue print with at least one of the human body system, the chief complaint and the list of pre-determined medical conditions within the one of the predefined areas.

16. The method of claim 13, further comprising storing the blue print in association with at least one level of a hierarchical structure comprising an evaluation type, a human body system, a chief complaint and the list of pre-determined medical conditions.

17. The method of claim 13, wherein retrieving the list of blue prints comprises populating the list of blue prints with those blue prints having control variables that match the pre-determined medical condition, and the method further comprises launching the blue print by selection of the condition from one of the selection view or the anatomical view when only one blue print is populated in the list of blue prints.

18. The method of claim 13, wherein retrieving from the database and displaying the list of pre-determined medical conditions comprises retrieving from the database and displaying a hierarchally related structure comprising an evaluation type, a human body system, a chief complaint and the list of pre-determined medical conditions.

19. An electronic medical records system, comprising:
   a database that includes an images library comprising a plurality of anatomical human images, a blue print library comprising a plurality of blue prints each capable of containing patient specific data, and a data structure library comprising a hierarchical structure of categories comprising an evaluation type category, a human body system category, a chief complaint category and a list of pre-determined medical conditions;
   a computer in communication with the database, the computer comprising a memory and a display;
   a selection view controller stored in the memory and executable by the computer to access the data structure library and the blue print library and to generate a selection screen for a particular patient on the display;
   the selection screen comprising an evaluation type indication, a human body system indication, a chief complaint indication and a medical condition associated with the chief complaint indication, the medical condition included in the pre-determined list of medical conditions and associated with a blue print containing patient specific data;
   an anatomy view controller stored in the memory and executable by the computer to generate an anatomy view for the particular patient, the anatomy view comprising an anatomical human image retrieved from the anatomical human images included in the database;

wherein the anatomical human image is divided into a plurality of predefined areas, and at least one of the predefined areas is associated with the medical condition and the blue print, and a blue print engine stored in the memory and executable by the controller to identify a list of blue prints associated with the medical condition, each of the blue prints configured to have a plurality of predetermined sentences formed in predetermined paragraphs, the predetermined sentences including fillable data locations mapped to control variables, wherein the blue print engine is further executable to launch the blue print, select control variables to populate the fillable data locations based on the patient specific data, and add the predetermined sentences containing the populated fillable data locations to the blueprint, a sentence structure of other blueprints that include fillable data locations mapped to the selected control variables also populated by the blue print engine.

20. The electronic medical records system of claim 19, wherein the blue print engine is further executable with the computer to generate a plurality of user entry formats to receive the patient specific data, the user entry formats comprising a blue print template, a key questions list, and an interactive question series.

21. The electronic medical records system of claim 19, wherein each of the blue prints corresponds to a predetermined medical condition included in the list of predetermined medical conditions, and selection of one of the predetermined medial conditions from either of the selection screen and the image screen results in display of the blue print in response to the list of blue prints only identifying the blue print.

22. The electronic medical records system of claim 19, wherein the anatomy view controller is configured display in the anatomy view for the particular patient an indicator in the one of the predefined areas, the indicator indicative of an office visit and a resulting blue print containing the patient specific data from the office visit.

23. The electronic medical records system of claim 19, wherein at least some of the plurality of predetermined sentences have a control set comprising a choice list containing control variables that are included in the list of pre-determined medical conditions.

* * * * *